United States Patent
Yamamoto et al.

(10) Patent No.: US 11,111,225 B2
(45) Date of Patent: Sep. 7, 2021

(54) CALIXARENE COMPOUND AND CURABLE COMPOSITION

(71) Applicant: DIC Corporation, Tokyo (JP)

(72) Inventors: Shinya Yamamoto, Sakura (JP); Masanori Miyamoto, Sakura (JP); Tomoyuki Imada, Ichihara (JP)

(73) Assignee: DIC Corporation, Tokyo (JP)

( * ) Notice: Subject to any disclaimer, the term of this patent is extended or adjusted under 35 U.S.C. 154(b) by 159 days.

(21) Appl. No.: 16/463,037

(22) PCT Filed: Nov. 16, 2017

(86) PCT No.: PCT/JP2017/041223
§ 371 (c)(1),
(2) Date: May 22, 2019

(87) PCT Pub. No.: WO2018/101057
PCT Pub. Date: Jun. 7, 2018

(65) Prior Publication Data
US 2019/0276421 A1   Sep. 12, 2019

(30) Foreign Application Priority Data
Dec. 1, 2016 (JP) ............................. JP2016-234109

(51) Int. Cl.
*C07D 303/23* (2006.01)
*C07C 43/225* (2006.01)
(Continued)

(52) U.S. Cl.
CPC ............ *C07D 303/23* (2013.01); *B29C 33/60* (2013.01); *C07C 43/225* (2013.01); *C07C 43/23* (2013.01);
(Continued)

(58) Field of Classification Search
CPC .. C07D 303/23; C07D 201/00; C07D 303/34; C07D 305/06; B29C 33/60;
(Continued)

(56) References Cited

U.S. PATENT DOCUMENTS 5,622,687 A * 4/1997 Krishnan ........... A61K 49/0442
424/9.33
2008/0115627 A1* 5/2008 Wang .................... C22B 11/048
75/718
(Continued)

FOREIGN PATENT DOCUMENTS

CN   101344737 A   1/2009
JP   10-260556 A   9/1998
(Continued)

OTHER PUBLICATIONS

M. Osipov et al., "Synthesis of deep-cavity fluorous calix[4]arenes as molecular recognition scaffolds," Beilstein Journal of Organic Chemistry, 2008, vol. 4, No. 36, pp. 1-6. (cited in the ISR).
(Continued)

*Primary Examiner* — John E Uselding
(74) *Attorney, Agent, or Firm* — Locke Lord LLP; James E. Armstrong, IV; Nicholas J. DiCeglie, Jr.

(57) ABSTRACT

A compound useful as a release agent, and a release agent, a curable composition, and a nanoimprint lithography resin material each containing the compound are provided. More specifically, a calixarene compound with a molecular structure represented by the following structural formula (1) and a composition containing the calixarene compound are provided.

(Continued)

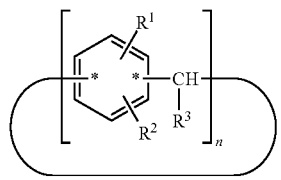

(1)

wherein $R^1$ denotes a structural moiety with a perfluoroalkyl group, $R^2$ denotes a hydrogen atom, a polar group, a polymerizable group, or a structural moiety with a polar group or a polymerizable group, $R^3$ denotes a hydrogen atom, an aliphatic hydrocarbon group that may have a substituent, or an aryl group that may have a substituent, n denotes an integer in the range of 2 to 10, and * denotes a bonding point with an aromatic ring.

6 Claims, 3 Drawing Sheets

(51) Int. Cl.

| | |
|---|---|
| C07C 49/83 | (2006.01) |
| C07C 69/653 | (2006.01) |
| C07C 69/712 | (2006.01) |
| C07C 323/16 | (2006.01) |
| C07D 305/06 | (2006.01) |
| C08L 33/10 | (2006.01) |
| C07F 9/38 | (2006.01) |
| C07C 43/23 | (2006.01) |
| C07C 327/06 | (2006.01) |
| C07F 9/12 | (2006.01) |
| C07C 323/12 | (2006.01) |
| C07C 59/66 | (2006.01) |
| C07F 9/09 | (2006.01) |
| C07F 7/04 | (2006.01) |
| B29C 33/60 | (2006.01) |
| C07D 303/34 | (2006.01) |
| C07F 1/00 | (2006.01) |
| H01L 21/027 | (2006.01) |
| C07D 201/00 | (2006.01) |
| C07D 209/48 | (2006.01) |

(52) U.S. Cl.
CPC .............. *C07C 49/83* (2013.01); *C07C 59/66* (2013.01); *C07C 69/653* (2013.01); *C07C 69/712* (2013.01); *C07C 323/12* (2013.01); *C07C 323/16* (2013.01); *C07C 327/06* (2013.01); *C07D 201/00* (2013.01); *C07D 209/48* (2013.01); *C07D 303/34* (2013.01); *C07D 305/06* (2013.01); *C07F 1/00* (2013.01); *C07F 7/04* (2013.01); *C07F 9/09* (2013.01); *C07F 9/12* (2013.01); *C07F 9/38* (2013.01); *C08L 33/10* (2013.01); *H01L 21/027* (2013.01); *C07C 2603/92* (2017.05); *H01L 21/0274* (2013.01)

(58) Field of Classification Search
CPC ....... C07C 43/225; C07C 43/23; C07C 59/66; C07C 69/653; C07C 49/83; C07C 69/712; C07C 323/12; C07C 323/16; C07C 327/06; C07F 1/00; C07F 1/04; C07F 9/09; C07F 9/12; C07F 9/38; C08L 33/10
See application file for complete search history.

(56) References Cited

U.S. PATENT DOCUMENTS

| | | | |
|---|---|---|---|
| 2009/0017395 A1 | 1/2009 | Ariyoshi et al. | |
| 2015/0140289 A1* | 5/2015 | Ferro | A61F 2/00 428/195.1 |
| 2015/0140729 A1* | 5/2015 | Ferro | H01L 51/0018 438/99 |
| 2017/0287694 A1* | 10/2017 | Robello | G03F 7/0388 |

FOREIGN PATENT DOCUMENTS

| | | |
|---|---|---|
| JP | 2002-302674 A | 10/2002 |
| JP | 2014-129517 A | 7/2014 |

OTHER PUBLICATIONS

O. M. Martin et al., "Synthesis and pH-dependent self-assembly of semifluorinated calix[4]arenes," Tetrahedron, vol. 63, 2007, pp. 5539-5547. (cited in the ISR).
O. M. Martin et al., "Solution self-assembly and solid state properties of fluorinated amphiphilic calix[4]arenes," Chemical Communications, 2005, pp. 4964-4966. (cited in the ISR).
J. D. Glennon et al., "Molecular baskets in Supercritical CO2," Analytical Chemistry, vol. 69, No. 11, 1997, pp. 2207-2212. (cited in the ISR).
W-Y Huang et al_, "Synthesis and properties of p-perfluoroalkylcalix[4]arenes," Chinese Journal of Chemistry, vol. 11, No. 4, 1993, pp. 370-375. (cited in the ISR).
J. P. Buttress et al., ""Janus" Calixarenes: Double-Sided Molecular Linkers for Facile, Multianchor Point, Multifunctional, Surface Modification," Langmuir, vol. 32, 2016, pp. 7806-7813 and Supporting Information (p. 1-44) (cited in the ISR).
M. Iqbal et al., "Calixarenes 21. The conformations and structures of the products of aroylation of the calix[4]arenes," Tetrahedron,vol. 43, No. 21, 1987, pp. 4917-4930. (cited in the ISR).
S. Buscemi, et al., "Lower rim arylation of calix[n]arenes with extended perfluorinated domains," Tetrahedron Letters, vol. 47, 2006, pp. 9049-9052. (cited in the ISR).
C.-Z. Zhang et al., "Significant Effect of Bromo Substituents on Nonlinear Optical Properties of Polymer and Chromophores," Journal of Physical Chemistry B, vol. 114, 2010, pp. 42-48. (cited in the ISR).
International Search Report dated Jan. 30, 2018, issued for PCT/JP2017/041223.
Japanese Translation of the Office Action dated Jul. 29, 2020, issued for the Chinese patent application No. 201780074462.X.

* cited by examiner

[Fig. 1]
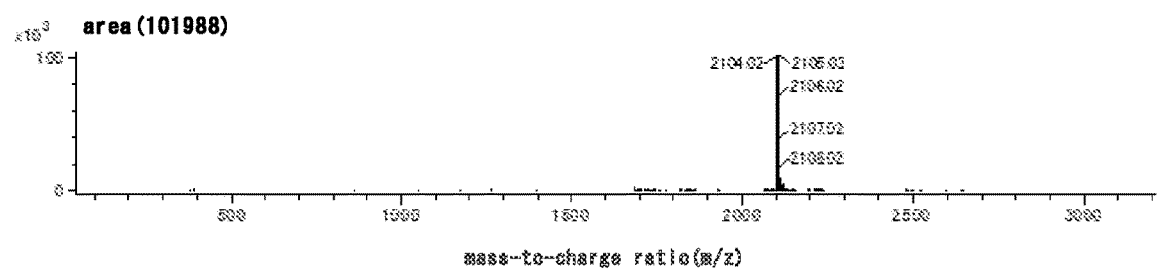
[Fig. 2]
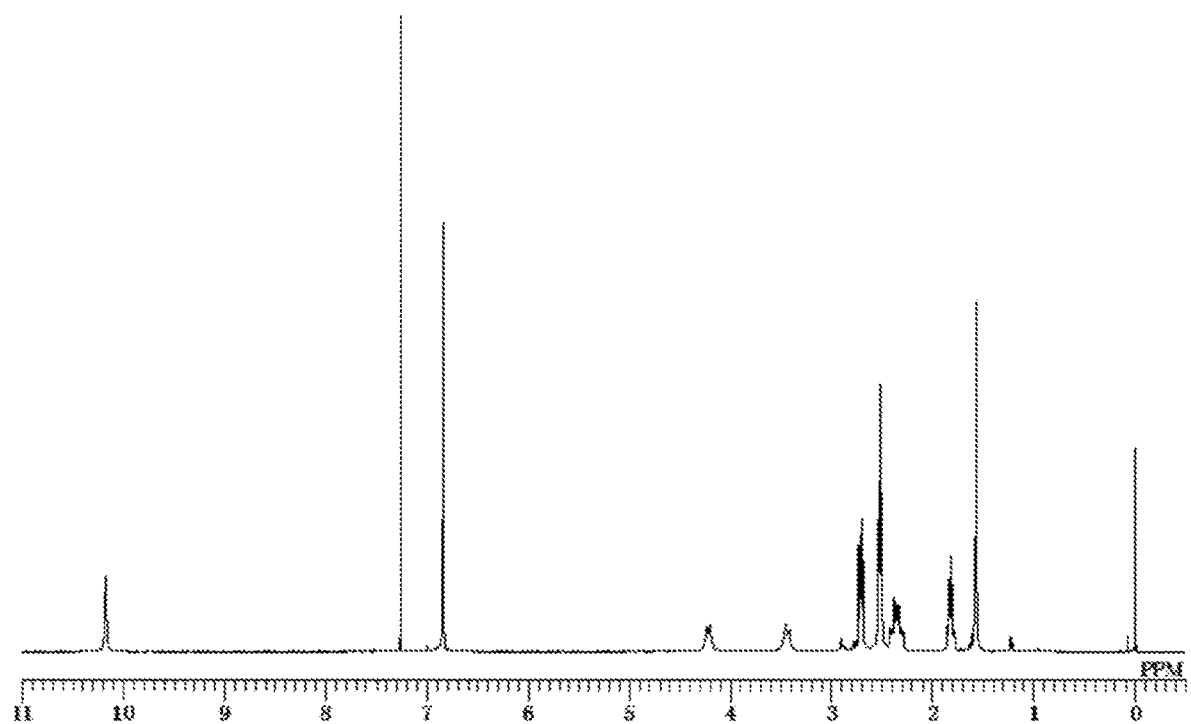

[Fig. 3]
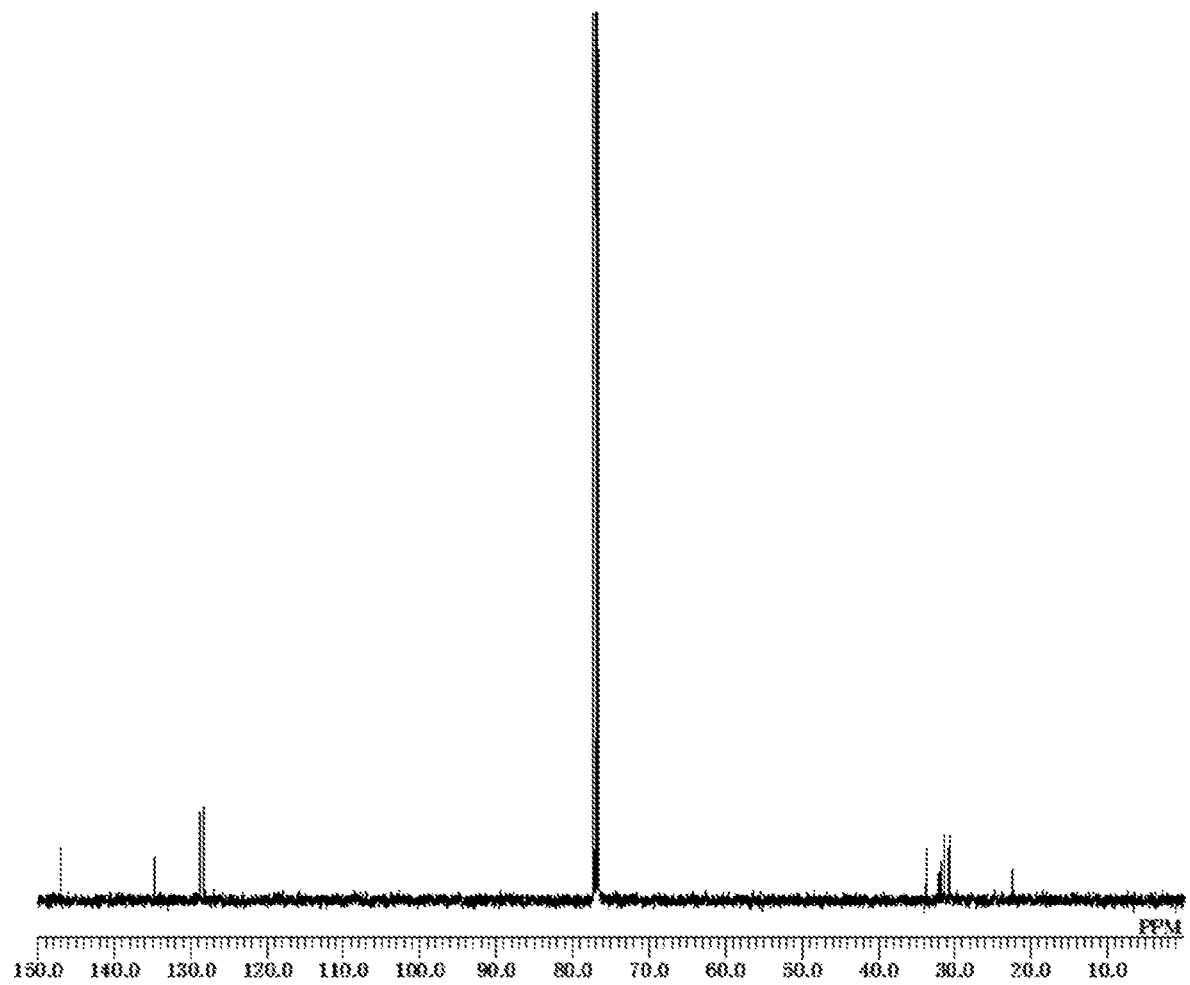

【Fig. 4】
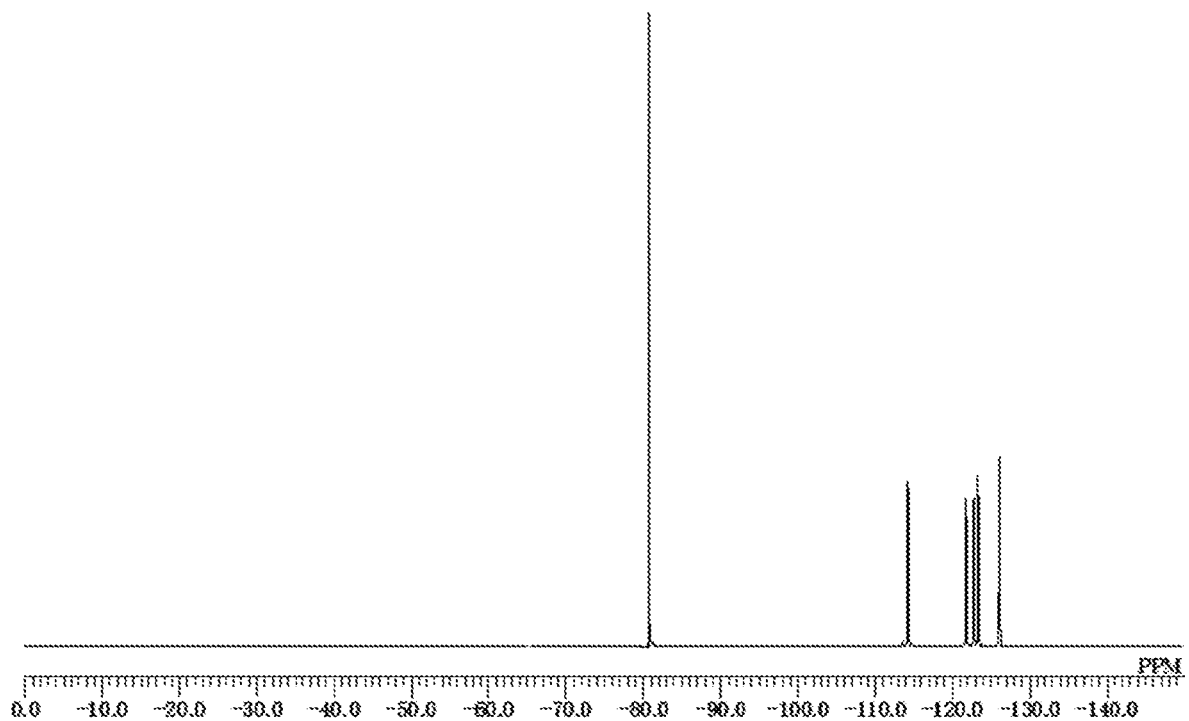

CALIXARENE COMPOUND AND CURABLE COMPOSITION

TECHNICAL FIELD

The present invention relates to a compound useful as a release agent, and a release agent, a curable composition, and a nanoimprint lithography resin material each containing the compound.

BACKGROUND ART

A technique of shaping a resin material with a forming die is utilized in a wide range of uses, including processing of a thermoplastic resin by injection molding and the latest nanoimprinting. In shaping techniques including the use of a forming die, the mold releasability of a resin molded product from the forming die is always an important issue, irrespective of the type of resin material and the shape of the forming die. A method of applying a release agent to a mold or a method of adding a release agent component to a resin material is known as a typical method for improving mold releasability, and a compound with a perfluoroalkyl group is widely utilized as a release agent (see Patent Literature 1, for example).

The nanoimprint technology, which is being put to practical use, has a particularly significant mold releasability problem due to the fine and complex shape of a forming die. In particular, in electric material applications, such as nanoimprint lithography, a slight pattern loss or pattern collapse can induce a critical defect in end products. In such situations, existing release agents cannot sufficiently meet the market demand, and there is a demand for the development of a release agent of a new molecular design.

CITATION LIST

Patent Literature

PTL 1: Japanese Unexamined Patent Application Publication No. 2014-129517

SUMMARY OF INVENTION

Technical Problem

Accordingly, it is an object of the present invention to provide a compound useful as a release agent, and a release agent, a curable composition, and a nanoimprint lithography resin material each containing the compound.

Solution to Problem

The present inventors have extensively studied to solve the above problems and completed the present invention by finding that a calixarene compound with a particular chemical structure has very high performance as a release agent, and a curable composition containing the calixarene compound has high mold releasability without losing applicability to various substrates.

Thus, the present invention relates to a calixarene compound with a molecular structure represented by the following structural formula (1).

[Chem. 1]

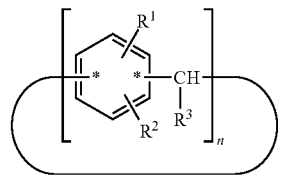

(1)

(wherein $R^1$ denotes a structural moiety with a perfluoroalkyl group, $R^2$ denotes a hydrogen atom, a polar group, a polymerizable group, or a structural moiety with a polar group or a polymerizable group, $R^3$ denotes a hydrogen atom, an aliphatic hydrocarbon group that may have a substituent, or an aryl group that may have a substituent, n denotes an integer in the range of 2 to 10, and * denotes a bonding point with an aromatic ring)

The present invention also relates to a release agent containing the calixarene compound.

The present invention also relates to a curable composition containing the calixarene compound and a curable resin material.

The present invention also relates to a nanoimprint lithography resin material containing the calixarene compound.

Advantageous Effects of Invention

The present invention can provide a calixarene compound useful as a release agent, and a release agent, a curable composition, and a nanoimprint lithography resin material each containing the compound.

BRIEF DESCRIPTION OF DRAWINGS

FIG. 1 is a FD-MS chart of a calixarene compound (1) prepared in Example 1.

FIG. 2 is a $^1$H-NMR chart of the calixarene compound (1) prepared in Example 1.

FIG. 3 is a $^{13}$C-NMR chart of the calixarene compound (1) prepared in Example 1.

FIG. 4 is a $^{19}$F-NMR chart of the calixarene compound (1) prepared in Example 1.

DESCRIPTION OF EMBODIMENTS

The present invention will be described in detail below.

A calixarene compound according to the present invention has a molecular structure represented by the following structural formula (1).

[Chem. 2]

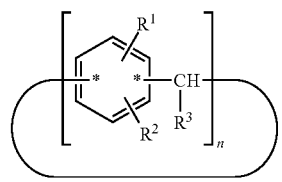

(1)

(wherein $R^1$ denotes a structural moiety with a perfluoroalkyl group, $R^2$ denotes a hydrogen atom, a polar group, a polymerizable group, or a structural moiety with a polar group or a polymerizable group, $R^3$ denotes a hydrogen atom, an aliphatic hydrocarbon group that may have a substituent, or an aryl group that may have a substituent, n denotes an integer in the range of 2 to 10, and * denotes a bonding point with an aromatic ring)

In the structural formula (1), n denotes an integer in the range of 2 to 10. In particular, n preferably denotes 4, 6, or 8 in terms of structural stability.

A calixarene compound according to the present invention has much better mold releasability than typical linear-polymer release agents because a structural moiety with a perfluoroalkyl group represented by $R^1$ is relatively densely packed. In the structural formula (1), the binding positions of $R^1$ and $R^2$ and the position of the bonding point represented by * are not particularly limited and may have any structure. In particular, those with a molecular structure represented by the following structural formula (1-1) or (1-2) are preferred because such a calixarene compound has higher performance as a release agent.

[Chem. 3]

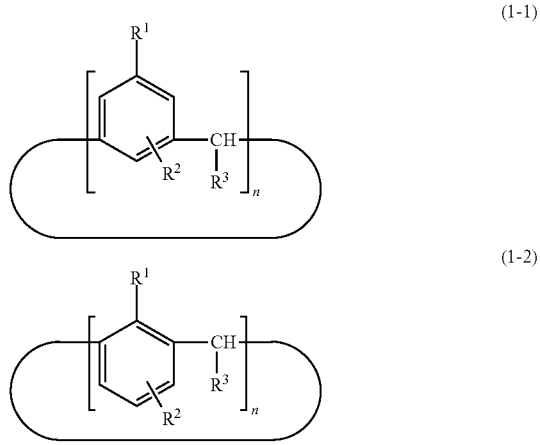

(1-1)

(1-2)

(wherein $R^1$ denotes a structural moiety with a perfluoroalkyl group, $R^2$ denotes a hydrogen atom, a polar group, a polymerizable group, or a structural moiety with a polar group or a polymerizable group, $R^3$ denotes a hydrogen atom, an aliphatic hydrocarbon group that may have a substituent, or an aryl group that may have a substituent, and n denotes an integer in the range of 2 to 10)

$R^1$ in the structural formula (1) denotes a structural moiety with a perfluoroalkyl group, which contributes to mold releasability when the calixarene compound is used as a release agent. Although the number of carbon atoms in the perfluoroalkyl group is not particularly limited, the number of carbon atoms preferably ranges from 1 to 6 from the perspective of biological safety. The structural moiety of $R^1$ other than the perfluoroalkyl group is not particularly limited and may have any structure. The specific structure of $R^1$ is represented by —X—$R^F$, for example, wherein $R^F$ denotes a perfluoroalkyl group.

For example, X is an alkylene group that may have a substituent, a (poly)alkylene ether structure, a (poly)alkylene thioether structure, a (poly)ester structure, a (poly)urethane structure, or a structural moiety composed thereof, and is preferably a (poly)alkylene ether chain or a (poly)alkylene thioether chain. A structure represented by the following structural formula (2) is preferred in terms of manufacturability.

[Chem. 4]

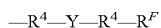 (2)

(wherein $R^4$ independently denotes a direct bond or an alkylene group having 1 to 6 carbon atoms, $R^F$ denotes a perfluoroalkyl group, and Y denotes a direct bond, a carbonyl group, an oxygen atom, or a sulfur atom)

$R^4$ in the structural formula (2) independently denotes an alkylene group having 1 to 6 carbon atoms. The alkylene group may be of a straight-chain type or may have a branched structure. The alkylene group is preferably of a straight-chain type because such a calixarene compound has high performance as a release agent.

$R^2$ in the structural formula (1) denotes a hydrogen atom, a polar group, a polymerizable group, or a structural moiety with a polar group or a polymerizable group. As described above, although the substitution position of $R^2$ on the aromatic ring is not particularly limited, when $R^2$ denotes a polar group, a polymerizable group, or a structural moiety with a polar group or a polymerizable group, the substitution position on the aromatic ring is preferably a para position relative to $R^1$. $R^2$ disposed at a para position relative to $R^1$, which has mold releasability, functions as a group with an affinity for a mold or a matrix component or reacts with a matrix component, thus resulting in a calixarene compound having higher performance as a release agent.

For example, $R^2$ in the structural formula (1) denotes, as a polar group, a hydroxy group, a thiol group, a phosphine oxide group, or a structural moiety with a polar group selected from a hydroxy group, an amino group, a carboxy group, a thiol group, a phosphate group, a phosphonate group, a phosphinate group, a phosphine oxide group, and an alkoxysilyl group. In the structural moiety with a polar group, the structural moiety except the polar group is not particularly limited and may have any structure. A specific example of the structural moiety with a polar group is represented by —O—X—$R^{P1}$, wherein $R^{P1}$ denotes the polar group. For example, X is an alkylene group that may have a substituent, or X is a (poly)alkylene ether structure, a (poly)alkylene thioether structure, a (poly)ester structure, a (poly)urethane structure, or a structural moiety composed thereof. In particular, X is preferably an alkylene group, more preferably an alkylene group having 1 to 6 carbon atoms. Thus, the structural moiety with a polar group is preferably a structural moiety represented by one of the following structural formulae (3-1) to (3-7), for example.

[Chem. 5]

 (3-1)

 (3-2)

 (3-3)

 (3-4)

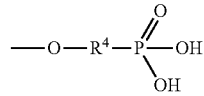 (3-5)

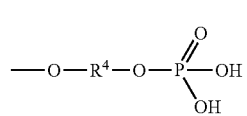 (3-6)

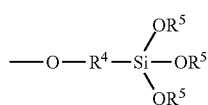 (3-7)

(wherein R⁴ independently denotes an alkylene group having 1 to 6 carbon atoms, and R5 denotes an alkyl group having 1 to 3 carbon atoms)

For example, $R^2$ in the structural formula (1) denotes, as a polymerizable group, a vinyloxy group, an ethynyloxy group, a (meth)acryloyloxy group, a glycidyloxy group, a (2-methyl)glycidyl group, a (2-methyl)glycidyloxy group, a 3-alkyloxetanylmethyloxy group, or a structural moiety with a polymerizable group selected from a vinyl group, a vinyloxy group, an ethynyl group, an ethynyloxy group, a (meth)acryloyl group, a (meth)acryloyloxy group, a glycidyl group, a glycidyloxy group, a (2-methyl)glycidyl group, a (2-methyl)glycidyloxy group, a 3-alkyloxetanylmethyl group, and a 3-alkyloxetanylmethyloxy group. In the structural moiety with a polymerizable group, the structural moiety except the polymerizable group is not particularly limited and may have any structure. A specific example of the structural moiety with a polymerizable group is represented by —O—X—$R^{P2}$, wherein $R^{P2}$ denotes the polymerizable group. For example, X is an alkylene group that may have a substituent, or X is a (poly)alkylene ether structure, a (poly)alkylene thioether structure, a (poly)ester structure, a (poly)urethane structure, or a structural moiety composed thereof. The structural moiety with a polymerizable group is preferably a structural moiety represented by one of the following structural formulae (4-1) to (4-8), for example.

[Chem. 6]

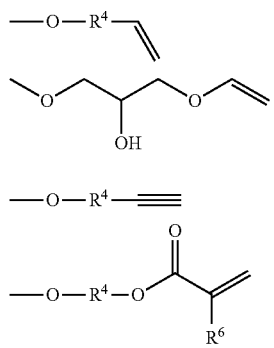

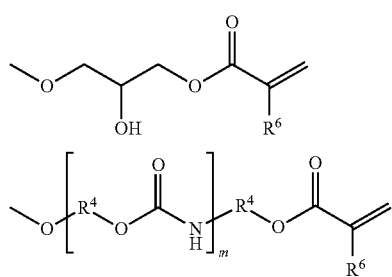

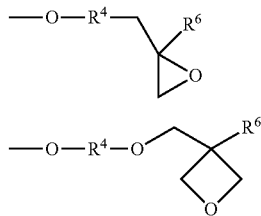

(wherein R⁴ independently denotes an alkylene group having 1 to 6 carbon atoms, and $R^6$ denotes a hydrogen atom or a methyl group)

$R^3$ in the structural formula (1) denotes a hydrogen atom, an aliphatic hydrocarbon group that may have a substituent, or an aryl group that may have a substituent. More specifically, $R^3$ may be an aliphatic hydrocarbon group selected from a methyl group, an ethyl group, a propyl group, an isopropyl group, a butyl group, a t-butyl group, a pentyl group, a hexyl group, a cyclohexyl group, a heptyl group, an octyl group, and a nonyl group, or a structural moiety in which one or more hydrogen atoms of these aliphatic hydrocarbon groups are substituted with a hydroxy group, an alkoxy group, a halogen atom, or the like; or a hydrocarbon group containing an aromatic ring, such as a phenyl group, a naphthyl group, or an anthryl group, or a structural moiety, such as a tolyl group or a xylyl group, that has a substituent, such as a hydroxy group, an alkyl group, an alkoxy group, or a halogen atom, on these aromatic nuclei. In particular, $R^3$ preferably denotes a hydrogen atom.

A calixarene compound according to the present invention may be produced by any method. A method for producing a calixarene compound according to the present invention will be described below.

For example, a calixarene compound according to the present invention can be produced by a method including a step of allowing an intermediate (A) represented by the following structural formula (5) to react with a halogenated allyl for allyl etherification (step 1), a step of transferring an allyl group by heating and stirring in the presence of an excessive amount of amine compound to produce an intermediate (B) represented by the following structural formula (6) (step 2), a step of introducing a perfluoroalkyl group (step 3), and a step of introducing a functional group corresponding to $R^2$, if necessary (step 4).

[Chem. 7]

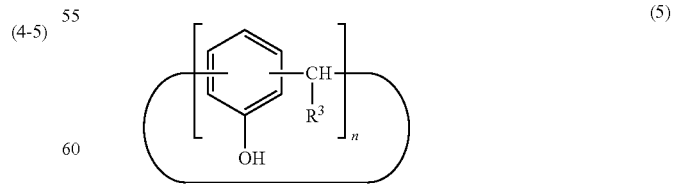 (5)

(wherein $R^3$ denotes a hydrogen atom, an aliphatic hydrocarbon group that may have a substituent, or an aryl group that may have a substituent, and n denotes an integer in the range of 2 to 10)

[Chem. 8]

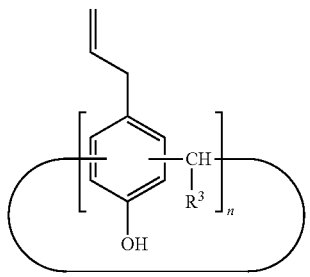

(6)

(wherein R³ denotes a hydrogen atom, an aliphatic hydrocarbon group that may have a substituent, or an aryl group that may have a substituent, and n denotes an integer in the range of 2 to 10)

The intermediate (A) represented by the structural formula (5) can be produced by a direct production method from phenol and an aldehyde compound or by a method of reacting a para-alkylphenol with an aldehyde compound to produce an intermediate (a) with a calixarene structure followed by a dealkylation reaction in the presence of phenol and aluminum chloride. In particular, the intermediate (A) can preferably be produced in high yield by reacting a para-alkylphenol with an aldehyde compound to produce an intermediate (a) with a calixarene structure followed by a dealkylation reaction in the presence of phenol and aluminum chloride.

The para-alkylphenol may be any phenol compound with an alkyl group at a para position. The alkyl group may be a methyl group, an ethyl group, a propyl group, a butyl group, a pentyl group, a hexyl group, a heptyl group, an octyl group, or a nonyl group, preferably a bulky group, such as a tert-butyl group, to produce the intermediate (a) in higher yield.

The aldehyde compound may be any compound that can cause a condensation reaction with the para-alkylphenol to form a calixarene structure, for example, formaldehyde, an aliphatic aldehyde compound, such as acetaldehyde or propionaldehyde, or an aromatic aldehyde compound, such as benzaldehyde or naphthaldehyde. These may be used alone or in combination. Among these, formaldehyde is preferably used due to its high reactivity. Formaldehyde may be used as an aqueous solution, formalin, or as a solid, paraformaldehyde.

For example, the reaction of a para-alkylphenol with an aldehyde compound can be performed in the presence of an acid or base catalyst at a temperature in the range of approximately 80° C. to 250° C. After the completion of the reaction, the product is preferably washed with water to produce an intermediate (a) of high purity.

As for the reaction ratio of the para-alkylphenol to the aldehyde compound, 0.6 to 2 moles of the aldehyde compound per mole of the para-alkylphenol is preferred to produce the intermediate (a) in high yield.

For example, the acid catalyst is an inorganic acid, such as hydrochloric acid, sulfuric acid, or phosphoric acid, an organic acid, such as methanesulfonic acid, para-toluenesulfonic acid, or oxalic acid, or a Lewis acid, such as boron trifluoride, anhydrous aluminum chloride, or zinc chloride. These may be used alone or in combination. The amount of acid catalyst to be added preferably ranges from 0.05 to 10 parts by mass per 100 parts by mass of the para-alkylphenol and the aldehyde compound.

The base catalyst may be any catalyst that acts as a catalyst, for example, an alkali metal hydroxide, such as sodium hydroxide, potassium hydroxide, or rubidium hydroxide, or an alkali metal carbonate, such as sodium carbonate or potassium carbonate. These may be used alone or in combination. The amount of base catalyst to be added preferably ranges from 0.01 to 1 part by mass per 100 parts by mass of the para-alkylphenol and the aldehyde compound.

The reaction between a para-alkylphenol and an aldehyde compound may be performed in an organic solvent. Examples of the organic solvent include ester solvents, such as ethyl acetate, methyl acetate, butyl acetate, methyl lactate, ethyl lactate, and butyl lactate; ketone solvents, such as acetone, methyl ethyl ketone, methyl isobutyl ketone, diacetone alcohol, and cyclohexane; alcohol solvents, such as methanol, ethanol, n-propanol, isopropanol, n-butanol, isobutanol, t-butanol, and ethylhexanol; ether solvents, such as dimethyl ether, diethyl ether, isopropyl ether, methyl cellosolve, cellosolve, butyl cellosolve, THF, dioxane, butyl carbitol, and biphenyl ether; and alcohol ether solvents, such as methoxyethanol, ethoxyethanol, and butoxyethanol. These may be used alone or in combination.

Dealkylation of the intermediate (a) can be performed, for example, by a method including adding the intermediate (a) and phenol to an organic solvent that is a poor solvent for the intermediate (a) and a good solvent for phenol, adding aluminum chloride to the organic solvent, and stirring the organic solvent. The reaction is preferably performed in an ice bath or at approximately room temperature.

The amount of phenol to be added preferably ranges from 1 to 2 moles per mole of the hydroxy group in the intermediate (a). The amount of aluminum chloride to be added preferably ranges from 1 to 2 moles per mole of the hydroxy group in the intermediate (a).

The organic solvent may be an aromatic hydrocarbon solvent, for example, benzene or an alkylbenzene, such as toluene or xylene.

After the completion of the reaction, the product is preferably purified by washing with water or by reprecipitation to produce an intermediate (A) of high purity.

The step of allowing the intermediate (A) to react with a halogenated allyl for allyl etherification (step 1) can be performed, for example, in the same manner as so-called Williamson ether synthesis, by stirring the intermediate (A) and the halogenated allyl in the presence of a basic catalyst at approximately room temperature. The reaction may be performed in an organic solvent. In particular, the reaction proceeds efficiently in a polar solvent, such as N-dimethylformamide, N-dimethylacetamide, or tetrahydrofuran. After the completion of the reaction, the product is preferably purified by washing with an alcohol solvent or the like.

In the step 2 after the step 1, the allyl etherification product in the step 1 is heated with stirring in the presence of an excessive amount of amine compound to transfer the allyl group, thereby producing the intermediate (B) represented by the structural formula (6).

Examples of the amine compound include tertiary amines, such as N,N-dimethylaniline, N,N-diethylaniline, N,N,N-trimethylamine, N,N,N-triethylamine, and diisopropylethylamine, and secondary amines, such as N,N-dimethylamine and N,N-diethylamine. These may be used alone or in combination.

After the completion of the reaction, the product is preferably purified by washing with an alcohol solvent or the like.

In the step 3, a perfluoroalkyl group is introduced into the intermediate (B) prepared in the step 2. Any perfluoroalkyl group introducing agent that can introduce a perfluoroalkyl group by reacting with the allyl group of the intermediate (B) may be used. A thiol compound with a perfluoroalkyl group has particularly high reactivity.

For example, the thiol compound is represented by the following structural formula (7).

[Chem. 9]

$$\text{HS—R}^7\text{—R}^F \qquad (7)$$

(wherein $R^7$ denotes an alkylene group having 1 to 6 carbon atoms, and $R^F$ denotes a perfluoroalkyl group)

Such thiol compounds may be used alone or in combination. The amount of thiol compound to be added is preferably excessively larger than the amount of the allyl group of the intermediate (B) and more preferably ranges from approximately 1 to 5 moles per mole of the allyl group.

For example, the reaction between the intermediate (B) and the thiol compound can be performed in the presence of a catalyst at a temperature in the range of approximately 50° C. to 80° C. The reaction may be performed in an organic solvent. Examples of the organic solvent include aromatic hydrocarbon solvents, such as toluene and xylene; alcohol solvents, such as methanol, ethanol, and isopropanol; and ketone solvents, such as methyl isobutyl ketone and methyl ethyl ketone.

The catalyst is 2,2'-azobis(2,4-dimethylvaleronitrile), for example. The amount of catalyst to be added preferably ranges from 0.05 to 0.5 moles per mole of the allyl group of the intermediate (B).

After the completion of the reaction, the product is preferably purified by washing with water or by reprecipitation.

The step 4 is performed to introduce a functional group corresponding to $R^2$ in the case that a compound represented by the structural formula (1) in which $R^2$ denotes a polar group, a polymerizable group, or a structural moiety with a polar group or a polymerizable group is produced. Any functional group introducing agent that can react with a phenolic hydroxy group may be used. In general, the target compound can efficiently be produced by a method of reacting a halide having a structural moiety corresponding to $R^2$ in the presence of a basic catalyst in the same manner as so-called Williamson ether synthesis.

As described above, a calixarene compound according to the present invention can be suitably used particularly in release agents, but its applications are not limited to the release agents. Examples of other applications include surface lubricating agents and leveling agents for coating agents, water repellents and oil repellents, and stain-proofing agents. These can be used instead of known compounds with a perfluoroalkyl group and perfluoropolyether compounds.

A calixarene compound according to the present invention for use in release agents may be used as a release agent that is applied to a forming die, or may be added to a resin material. As described above, a calixarene compound according to the present invention is also effective as a surface lubricating agent, a leveling agent, a water repellent, an oil repellent, or a stain-proofing agent. Thus, when a calixarene compound according to the present invention is added to a resin material, the calixarene compound can perform satisfactorily without such agents and is valuable in this respect.

A curable composition containing a calixarene compound according to the present invention may be of any curing type, such as thermosetting or active energy beam curable. In the case that the curable composition is a thermosetting composition, a curable resin material in the composition may be a urethane resin, an epoxy resin, a phenolic resin, a urea resin, a melamine resin, an unsaturated polyester resin, or a silicon resin.

In the case that the curable composition is an active energy beam curable composition, a curable resin material in the composition may be a compound with a (meth)acryloyl group. Examples of the compound with a (meth)acryloyl group include mono(meth)acrylate compounds and modified compounds thereof (R1), aliphatic hydrocarbon type poly(meth)acrylate compounds and modified compounds thereof (R2), alicyclic poly(meth)acrylate compounds and modified compounds thereof (R3), aromatic poly(meth)acrylate compounds and modified compounds thereof (R4), (meth)acrylate resins with a silicone chain and modified compounds thereof (R5), epoxy (meth)acrylate resins and modified resins thereof (R6), urethane (meth)acrylate resins and modified resins thereof (R7), acrylic (meth)acrylate resins and modified resins thereof (R8), and dendrimer type (meth)acrylate resins and modified resins thereof (R9).

Examples of the mono(meth)acrylate compounds and modified compounds thereof (R1) include aliphatic mono(meth)acrylate compounds, such as methyl (meth)acrylate, ethyl (meth)acrylate, hydroxyethyl (meth)acrylate, propyl (meth)acrylate, hydroxypropyl (meth)acrylate, butyl (meth)acrylate, and 2-ethylhexyl (meth)acrylate; alicyclic mono(meth)acrylate compounds, such as cyclohexyl (meth)acrylate, isobornyl (meth)acrylate, and adamantyl mono(meth)acrylate; heterocyclic mono(meth)acrylate compounds, such as glycidyl (meth)acrylate and tetrahydrofurfuryl acrylate; aromatic mono(meth)acrylate compounds, such as phenyl (meth)acrylate, benzyl (meth)acrylate, phenoxy (meth)acrylate, phenoxyethyl (meth)acrylate, phenoxyethoxyethyl (meth)acrylate, 2-hydroxy-3-phenoxypropyl (meth)acrylate, phenylphenol (meth)acrylate, phenylbenzyl (meth)acrylate, phenoxybenzyl (meth)acrylate, benzylbenzyl (meth)acrylate, phenylphenoxyethyl (meth)acrylate, and para-cumylphenol (meth)acrylate; mono(meth)acrylate compounds, such as compounds represented by the following structural formula (8): (poly)oxyalkylene modified compounds having a (poly)oxyalkylene chain, such as a (poly)oxyethylene chain, a (poly)oxypropylene chain, or a (poly)oxytetramethylene chain, in a molecular structure of the above various mono(meth)acrylate compounds; and lactone modified compounds having a (poly)lactone structure in a molecular structure of the above various mono(meth)acrylate compounds.

[Chem. 10]

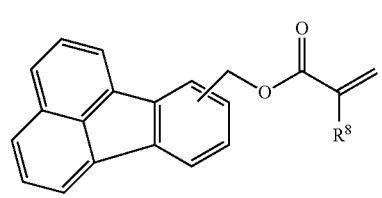

(8)

(wherein $R^8$ denotes a hydrogen atom or a methyl group)

Examples of the aliphatic hydrocarbon type poly(meth)acrylate compounds and modified compounds thereof (R2) include aliphatic di(meth)acrylate compounds, such as ethylene glycol di(meth)acrylate, propylene glycol di(meth)

acrylate, butanediol di(meth)acrylate, hexanediol di(meth) acrylate, and neopentyl glycol di(meth)acrylate; aliphatic tri(meth)acrylate compounds, such as trimethylolpropane tri(meth)acrylate, glycerin tri(meth)acrylate, pentaerythritol tri(meth)acrylate, ditrimethylolpropane tri(meth)acrylate, and dipentaerythritol tri(meth)acrylate; tetra or higher functional aliphatic poly(meth)acrylate compounds, such as pentaerythritol tetra(meth)acrylate, ditrimethylolpropane tetra (meth)acrylate, dipentaerythritol tetra(meth)acrylate, dipentaerythritol penta(meth)acrylate, and dipentaerythritol hexa(meth)acrylate; (poly)oxyalkylene modified compounds having a (poly)oxyalkylene chain, such as a (poly) oxyethylene chain, a (poly)oxypropylene chain, or a (poly) oxytetramethylene chain, in a molecular structure of the above various aliphatic hydrocarbon type poly(meth)acrylate compounds; and lactone modified compounds having a (poly)lactone structure in a molecular structure of the above various aliphatic hydrocarbon type poly(meth)acrylate compounds.

Examples of the alicyclic poly(meth)acrylate compounds and modified compounds thereof (R3) include alicyclic di(meth)acrylate compounds, such as 1,4-cyclohexane dimethanol di(meth)acrylate, norbornane di(meth)acrylate, norbornane dimethanol di(meth)acrylate, dicyclopentanyl di(meth)acrylate, and tricyclodecane dimethanol di(meth) acrylate; (poly)oxyalkylene modified compounds having a (poly)oxyalkylene chain, such as a (poly)oxyethylene chain, a (poly)oxypropylene chain, or a (poly)oxytetramethylene chain, in a molecular structure of the above various alicyclic poly(meth)acrylate compounds; and lactone modified compounds having a (poly)lactone structure in a molecular structure of the above various alicyclic poly(meth)acrylate compounds.

Examples of the aromatic poly(meth)acrylate compounds and modified compounds thereof (R4) include aromatic di(meth)acrylate compounds, such as biphenol di(meth) acrylate, bisphenol di(meth)acrylate, bicarbazole compounds represented by the following structural formula (9), and fluorene compounds represented by the following structural formula (10-1) or (10-2);

[Chem. 11]

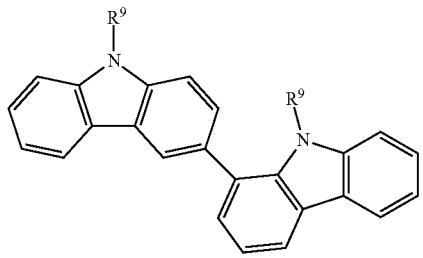

(9)

[wherein $R^9$ independently denotes a (meth)acryloyl group, a (meth)acryloyloxy group, or a (meth)acryloyloxyalkyl group]

[Chem. 12]

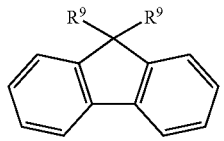

(10-1)

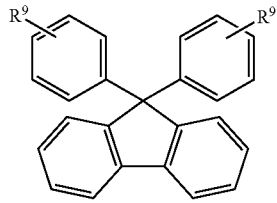

(10-2)

[wherein $R^9$ independently denotes a (meth)acryloyl group, a (meth)acryloyloxy group, or a (meth)acryloyloxyalkyl group]

(poly)oxyalkylene modified compounds having a (poly) oxyalkylene chain, such as (poly)oxyethylene chain, a (poly) oxypropylene chain, or a (poly)oxytetramethylene chain, in a molecular structure of the above various aromatic poly (meth)acrylate compounds; and lactone modified compounds having a (poly)lactone structure in a molecular structure of the above various aromatic poly(meth)acrylate compounds.

The (meth)acrylate resins with a silicone chain and modified compounds thereof (R5) vary widely and may be any compounds having a silicone chain and a (meth)acryloyl group in their molecular structures. The (meth)acrylate resins with a silicone chain and modified compounds thereof (R5) may be produced by any method. Specific examples of the (meth)acrylate resins with a silicone chain and modified compounds thereof (R5) include reaction products of a silicone compound with an alkoxysilane group and a (meth) acrylate compound with a hydroxy group.

Examples of commercial products of the silicone compound with an alkoxysilane group include "X-40-9246" (alkoxy group content: 12% by mass), "KR-9218" (alkoxy group content: 15% by mass), "X-40-9227" (alkoxy group content: 15% by mass), "KR-510" (alkoxy group content: 17% by mass), "KR-213" (alkoxy group content: 20% by mass), "X-40-9225" (alkoxy group content: 24% by mass), "X-40-9250" (alkoxy group content: 25% by mass), "KR-500" (alkoxy group content: 28% by mass), "KR-401N" (alkoxy group content: 33% by mass), and "KR-515" (alkoxy group content: 40% by mass), "KC-89S" (alkoxy group content: 45% by mass), each manufactured by Shin-Etsu Chemical Co., Ltd. These may be used alone or in combination. In particular, the alkoxy group content preferably ranges from 15% to 40% by mass. When at least two silicone compounds are used in combination, the average alkoxy group content preferably ranges from 15% to 40% by mass.

Examples of the (meth)acrylate compound with a hydroxy group include (meth)acrylate compounds with a hydroxy group, such as hydroxyethyl (meth)acrylate, hydroxypropyl (meth)acrylate, trimethylolpropane di(meth)acrylate, pentaerythritol tri(meth)acrylate, ditrimethylolpropane tri (meth)acrylate, and dipentaerythritol penta(meth)acrylate; (poly)oxyalkylene modified compounds having a (poly) oxyalkylene chain, such as a (poly)oxyethylene chain, a (poly)oxypropylene chain, or a (poly)oxytetramethylene chain, in a molecular structure of the above various (meth) acrylate compounds with a hydroxy group; and lactone modified compounds having a (poly)lactone structure in a molecular structure of the above various (meth)acrylate compounds with a hydroxy group.

The (meth)acrylate resins with a silicone chain and modified compounds thereof (R5) may also be commercial products, for example, silicone oils having a (meth)acryloyl group on one end, such as "X-22-174ASX" (methacryloyl group equivalent: 900 g/equivalent), "X-22-174BX" (methacryloyl group equivalent: 2,300 g/equivalent), "X-22-174DX" (methacryloyl group equivalent: 4,600 g/equivalent), "KF-2012" (methacryloyl group equivalent: 4,600 g/equivalent), "X-22-2426" (methacryloyl group equivalent: 12,000 g/equivalent), "X-22-2404" (methacryloyl group equivalent: 420 g/equivalent), and "X-22-2475" (methacryloyl group equivalent: 420 g/equivalent), each manufactured by Shin-Etsu Chemical Co., Ltd.; silicone oils having a (meth)acryloyl group on both ends, such as "X-22-164" (methacryloyl group equivalent: 190 g/equivalent), "X-22-164AS" (methacryloyl group equivalent: 450 g/equivalent), "X-22-164A" (methacryloyl group equivalent: 860 g/equivalent), "X-22-164B" (methacryloyl group equivalent: 1,600 g/equivalent), "X-22-164C" (methacryloyl group equivalent: 2,400 g/equivalent), "X-22-164E" (methacryloyl group equivalent: 3,900 g/equivalent), and "X-22-2445" (acryloyl group equivalent: 1,600 g/equivalent), each manufactured by Shin-Etsu Chemical Co., Ltd.; and oligomer type silicone compounds having a plurality of (meth) acryloyl groups in one molecule, such as "KR-513" (methacryloyl group equivalent: 210 g/equivalent) and "–40-9296" (methacryloyl group equivalent: 230 g/equivalent) each manufactured by Shin-Etsu Chemical Co., Ltd, and "AC-SQ TA-100" (acryloyl group equivalent: 165 g/equivalent), "AC-SQ SI-20" (acryloyl group equivalent: 207 g/equivalent), "MAC-SQ TM-100" (methacryloyl group equivalent: 179 g/equivalent), "MAC-SQ SI-20" (methacryloyl group equivalent: 224 g/equivalent), and "MAC-SQ HDM" (methacryloyl group equivalent: 239 g/equivalent), each manufactured by Toagosei Co., Ltd.

The (meth)acrylate resins with a silicone chain and modified compounds thereof (R5) preferably have a weight-average molecular weight (Mw) in the range of 1,000 to 10,000, more preferably 1,000 to 5,000. The (meth)acrylate resins with a silicone chain and modified compounds thereof (R5) preferably have a (meth)acryloyl group equivalent in the range of 150 to 5,000 g/equivalent, more preferably 150 to 2,500 g/equivalent.

Examples of the epoxy (meth)acrylate resins and modified resins thereof (R6) include reaction products of an epoxy resin and a (meth)acrylic acid or its anhydride. Examples of the epoxy resin include diglycidyl ethers of divalent phenols, such as hydroquinone and catechol; diglycidyl ethers of biphenol compounds, such as 3,3'-biphenyldiol and 4,4'-biphenyldiol; bisphenol type epoxy resins, such as bisphenol A type epoxy resins, bisphenol B type epoxy resins, bisphenol F type epoxy resins, and bisphenol S type epoxy resins; polyglycidyl ethers of naphthol compounds, such as 1,4-naphthalenediol, 1,5-naphthalenediol, 1,6-naphthalenediol, 2,6-naphthalenediol, 2,7-naphthalenediol, binaphthol, and bis(2,7-dihydroxynaphthyl)methane; triglycidyl ethers, such as 4,4',4"-methylidynetrisphenol; novolak type epoxy resins, such as phenol novolak type epoxy resins and cresol novolak resins; (poly)oxyalkylene modified compounds having a (poly)oxyalkylene chain, such as a (poly)oxyethylene chain, a (poly)oxypropylene chain, or a (poly)oxytetramethylene chain, in a molecular structure of the above various epoxy resins; and lactone modified compounds having a (poly) lactone structure in a molecular structure of the above various epoxy resins.

Examples of the urethane (meth)acrylate resins and modified resins thereof (R7) include reaction products of various polyisocyanate compounds, (meth)acrylate compounds with a hydroxy group, and if necessary various polyol compounds. Examples of the polyisocyanate compounds include aliphatic diisocyanate compounds, such as butane diisocyanate, hexamethylene diisocyanate, 2,2,4-trimethylhexamethylene diisocyanate, and 2,4,4-trimethylhexamethylene diisocyanate; alicyclic diisocyanate compounds, such as norbornane diisocyanate, isophorone diisocyanate, hydrogenated xylylene diisocyanate, and hydrogenated diphenylmethane diisocyanate; aromatic diisocyanate compounds, such as tolylene diisocyanate, xylylene diisocyanate, tetramethylxylylene diisocyanate, diphenylmethane diisocyanate, and 1,5-naphthalene diisocyanate; polymethylene polyphenyl polyisocyanates with a repeating structure represented by the following structural formula (11); and isocyanurate modified compounds, biuret modified compounds, and allophanate modified compounds thereof.

[Chem. 13]

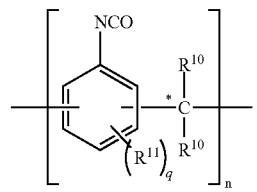

(11)

[$R^{10}$ independently denotes a hydrogen atom or a hydrocarbon group having 1 to 6 carbon atoms. $R^{11}$ independently denotes an alkyl group having 1 to 4 carbon atoms or a bonding point to be bonded to a structural moiety represented by the structural formula (11) via a methylene group marked with *. q denotes an integer of 0 or 1 to 3, and p denotes an integer of 1 or more.]

Examples of the (meth)acrylate compound with a hydroxy group include (meth)acrylate compounds with a hydroxy group, such as hydroxyethyl (meth)acrylate, hydroxypropyl (meth)acrylate, trimethylolpropane di(meth)acrylate, pentaerythritol tri(meth)acrylate, ditrimethylolpropane tri (meth)acrylate, and dipentaerythritol penta(meth)acrylate; (poly)oxyalkylene modified compounds having a (poly) oxyalkylene chain, such as a (poly)oxyethylene chain, a (poly)oxypropylene chain, or a (poly)oxytetramethylene chain, in a molecular structure of the above various (meth) acrylate compounds with a hydroxy group; and lactone modified compounds having a (poly)lactone structure in a molecular structure of the above various (meth)acrylate compounds with a hydroxy group.

Examples of the polyol compounds include aliphatic polyol compounds, such as ethylene glycol, propylene glycol, butanediol, hexanediol, glycerin, trimethylolpropane, ditrimethylolpropane, pentaerythritol, and dipentaerythritol; aromatic polyol compounds, such as biphenol and bisphenol; (poly)oxyalkylene modified compounds having a (poly) oxyalkylene chain, such as a (poly)oxyethylene chain, a (poly)oxypropylene chain, or a (poly)oxytetramethylene chain, in a molecular structure of the above various polyol compounds; and lactone modified compounds having a (poly)lactone structure in a molecular structure of the above various polyol compounds.

Examples of the acrylic (meth)acrylate resins and modified resins thereof (R8) include those produced by introducing a (meth)acryloyl group into an acrylic resin intermediate produced by polymerization of an essential component, a (meth)acrylate monomer (α) with a reactive functional group, such as a hydroxy group, a carboxy group, an isocyanate group, or a glycidyl group. The (meth)acryloyl group is introduced into the acrylic resin intermediate by reacting the acrylic resin intermediate with a (meth)acrylate monomer (β) with a reactive functional group that can react with these functional groups.

For example, the (meth)acrylate monomer (α) with a reactive functional group is a (meth)acrylate monomer with a hydroxy group, such as hydroxyethyl (meth)acrylate or hydroxypropyl (meth)acrylate; a (meth)acrylate monomer with a carboxy group, such as (meth)acrylic acid; a (meth)acrylate monomer with an isocyanate group, such as 2-acryloyloxyethyl isocyanate, 2-methacryloyloxyethyl isocyanate, or 1,1-bis(acryloyloxymethyl)ethyl isocyanate; or a (meth)acrylate monomer with a glycidyl group, such as glycidyl (meth)acrylate or 4-hydroxybutyl acrylate glycidyl ether. These may be used alone or in combination.

The acrylic resin intermediate may also be produced by polymerization of the (meth)acrylate monomer (α) and if necessary another compound with a polymerizable unsaturated group. Examples of the other compound with a polymerizable unsaturated group include alkyl (meth)acrylates, such as methyl (meth)acrylate, ethyl (meth)acrylate, propyl (meth)acrylate, butyl (meth)acrylate, and 2-ethylhexyl (meth)acrylate; cyclic (meth)acrylates, such as cyclohexyl (meth)acrylate, isobornyl (meth)acrylate, and dicyclopentanyl (meth)acrylate; (meth)acrylates with an aromatic ring, such as phenyl (meth)acrylate, benzyl (meth)acrylate, and phenoxyethyl acrylate; (meth)acrylates with a silyl group, such as 3-methacryloxypropyltrimethoxysilane; and styrene derivatives, such as styrene, α-methylstyrene, and chlorostyrene. These may be used alone or in combination.

The (meth)acrylate monomer (β) may be any (meth)acrylate monomer that can react with the reactive functional group of the (meth)acrylate monomer (α), and the following combinations are preferred in terms of reactivity. When the (meth)acrylate monomer (α) is the (meth)acrylate with a hydroxy group, the (meth)acrylate monomer (β) is preferably a (meth)acrylate with an isocyanate group. When the (meth)acrylate monomer (α) is the (meth)acrylate with a carboxy group, the (meth)acrylate monomer (β) is preferably the (meth)acrylate with a glycidyl group. When the (meth)acrylate monomer (α) is the (meth)acrylate with an isocyanate group, the (meth)acrylate monomer (β) is preferably the (meth)acrylate with a hydroxy group. When the (meth)acrylate monomer (α) is the (meth)acrylate with a glycidyl group, the (meth)acrylate monomer (β) is preferably the (meth)acrylate with a carboxy group.

The acrylic (meth)acrylate resins and modified resins thereof (R8) preferably have a weight-average molecular weight (Mw) in the range of 5,000 to 50,000. The acrylic (meth)acrylate resins and modified resins thereof (R8) preferably have a (meth)acryloyl group equivalent in the range of 200 to 300 g/equivalent.

The dendrimer type (meth)acrylate resins and modified resins thereof (R9) refer to resins with a regular multibranched structure and with a (meth)acryloyl group at the end of each branched chain and are also referred to as hyperbranched or star polymers. Examples of such compounds include, but are not limited to, those represented by the following structural formulae (12-1) to (12-8). Any resins with a regular multibranched structure and with a (meth)acryloyl group at the end of each branched chain may be used.

[Chem. 14]

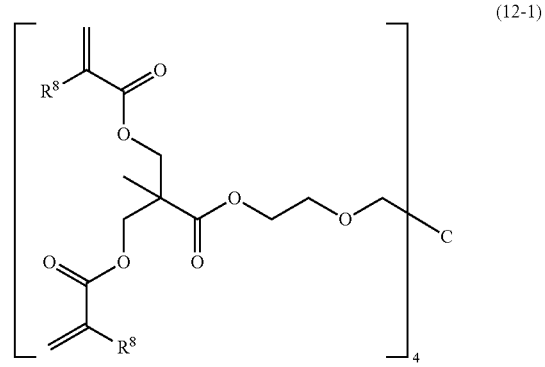

(12-1)

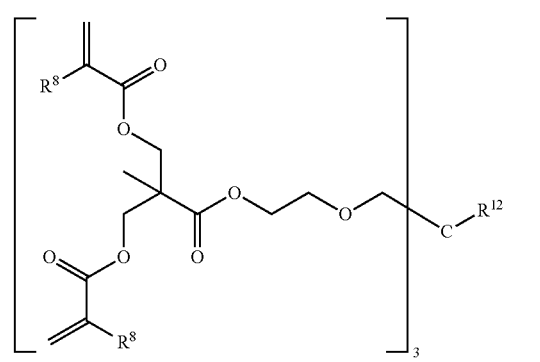

(12-2)

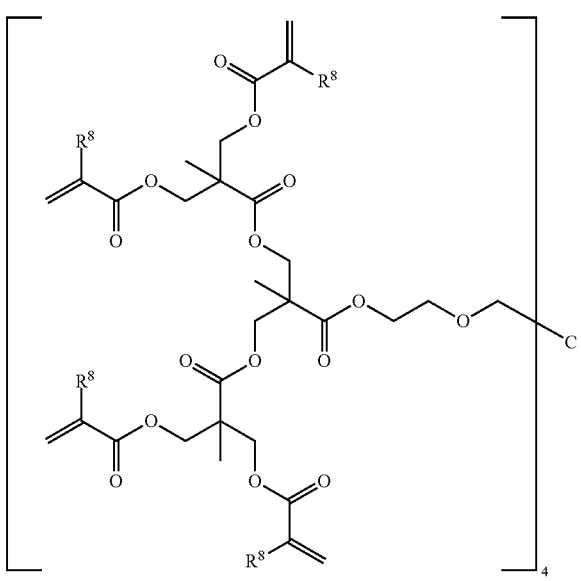

(12-3)

(12-4)
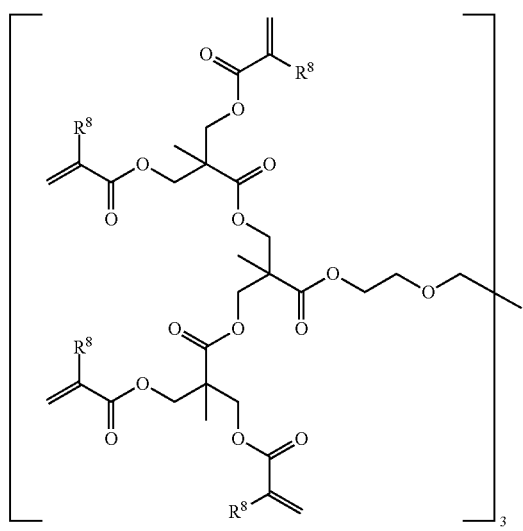

[Chem. 15]

(12-5)
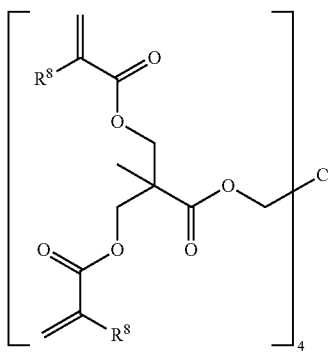

(12-6)
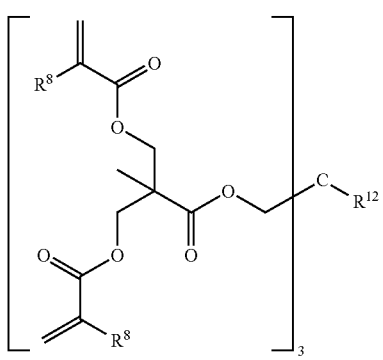

(12-7)
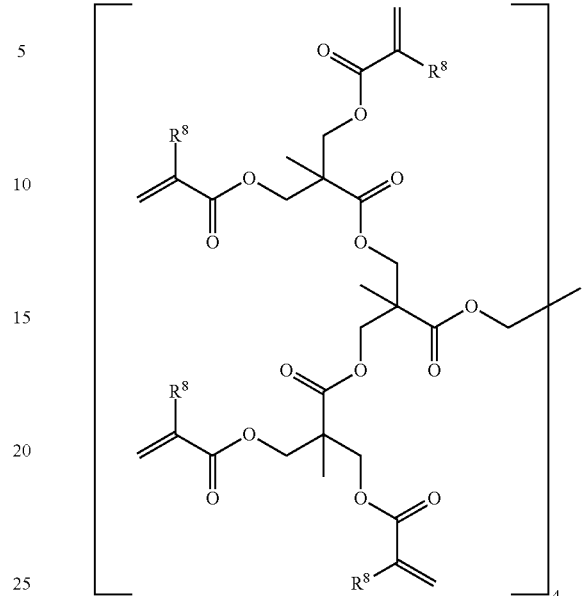

(12-8)
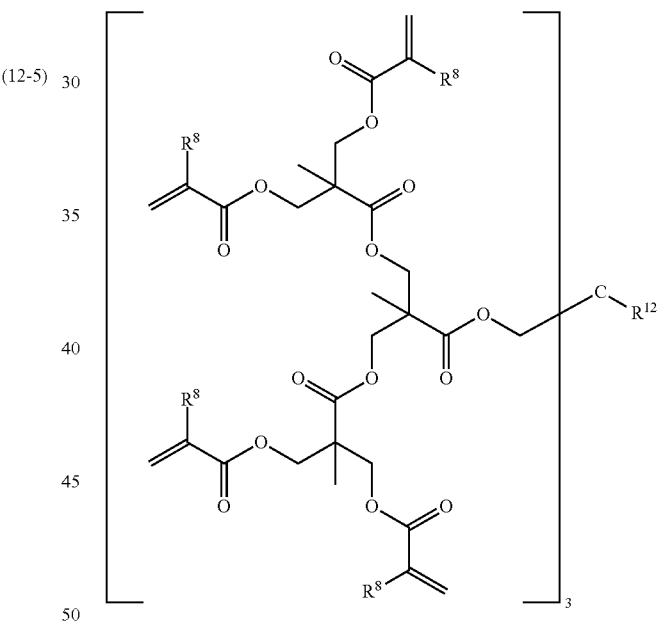

(wherein $R^8$ denotes a hydrogen atom or a methyl group, and $R^{12}$ denotes a hydrocarbon group having 1 to 4 carbon atoms)

Such dendrimer type (meth)acrylate resins and modified resins thereof (R9) may be commercial products, for example, "Viscoat #1000" [weight-average molecular weight (Mw): 1,500 to 2,000, average number of (meth)acryloyl groups per molecule: 14], "Viscoat 1020" [weight-average molecular weight (Mw): 1,000 to 3,000], "SIRIUS 501" [weight-average molecular weight (Mw): 15,000 to 23,000], each manufactured by Osaka Organic Chemical Industry Ltd., "SP-1106" manufactured by MIWON [weight-average molecular weight (Mw): 1,630, average number of (meth)acryloyl groups per molecule: 18], "CN2301", "CN2302" [average number of (meth)acryloyl groups per molecule: 16], "CN2303" [average number of (meth)acryloyl groups per molecule: 6], "CN2304" [average number of (meth)acryloyl groups per molecule: 18], each manufactured by SARTOMER, "Esdrimer HU-22" manufactured by Nippon Steel & Sumikin Chemical Co., Ltd., "A-HBR-5" manufactured by Shin Nakamura Chemical Co., Ltd., "New Frontier R-1150" manufactured by Dai-ichi Kogyo Seiyaku Co., Ltd., and "Hypertech UR-101" manufactured by Nissan Chemical Industries, Ltd.

The dendrimer type (meth)acrylate resins and modified resins thereof (R9) preferably have a weight-average molecular weight (Mw) in the range of 1,000 to 30,000. The average number of (meth)acryloyl groups per molecule preferably ranges from 5 to 30.

The compound with a (meth)acryloyl group is appropriately chosen for each intended use. In particular, when the curable composition is used to form a fine shape, such as in nanoimprint lithography applications, the solventless composition viscosity measured with an E-type rotational viscometer is preferably 1,000 mPa·s or less, more preferably 100 mPa·s or less.

When the curable composition is an active energy beam curable composition, the curable composition preferably contains a photopolymerization initiator. The photopolymerization initiator can be chosen from appropriate photopolymerization initiators in accordance with the type of active energy beam to be emitted. Specific examples of the photopolymerization initiator include alkylphenone photopolymerization initiators, such as 1-hydroxy-cyclohexyl-phenyl-ketone, 2-benzyl-2-dimethylamino-1-(4-morpholinophenyl)-butanone-1, and 2-(dimethylamino)-2-[(4-methylphenyl)methyl]-1-[4-(4-morpholinyl)phenyl]-1-butanone; acylphosphine oxide photopolymerization initiators, such as 2,4,6-trimethylbenzoyl-diphenyl-phosphine oxide; and intramolecular hydrogen abstraction type photopolymerization initiators, such as benzophenone compounds. These may be used alone or in combination.

Examples of commercial products of the photopolymerization initiator include "IRGACURE 127", "IRGACURE 184", "IRGACURE 250", "IRGACURE 270", "IRGACURE 290", "IRGACURE 369E", "IRGACURE 379EG", "IRGACURE 500", "IRGACURE 651", "IRGACURE 754", "IRGACURE 819", "IRGACURE 907", "IRGACURE 1173", "IRGACURE 2959", "IRGACURE MBF", "IRGACURE TPO", "IRGACURE OXE 01", and "IRGACURE OXE 02", each manufactured by BASF.

The amount of the photopolymerization initiator to be used preferably ranges from 0.05 to 20 parts by mass, more preferably 0.1 to 10 parts by mass, per 100 parts by mass of the components of the active energy beam curable composition except organic solvents.

A curable composition according to the present invention may be diluted with an organic solvent. The organic solvent may be an alkylene glycol monoalkyl ether, such as ethylene glycol monomethyl ether, ethylene glycol monoethyl ether, ethylene glycol monopropyl ether, or ethylene glycol monobutyl ether, propylene glycol monomethyl ether; a dialkylene glycol dialkyl ether, such as diethylene glycol dimethyl ether, diethylene glycol diethyl ether, diethylene glycol dipropyl ether, or diethylene glycol dibutyl ether; an alkylene glycol alkyl ether acetate, such as ethylene glycol monomethyl ether acetate, ethylene glycol monoethyl ether acetate, or propylene glycol monomethyl ether acetate; a ketone compound, such as acetone, methyl ethyl ketone, cyclohexanone, or methyl amyl ketone; a cyclic ether, such as dioxane; or an ester compound, such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, or ethyl acetoacetate. These may be used alone or in combination. The amount of organic solvent to be added is appropriately adjusted for the desired composition viscosity or the like.

A curable composition according to the present invention may contain various additive agents depending on the desired performance. Examples of the additive agents include ultraviolet absorbers, antioxidants, photosensitizers, silicone additive agents, silane coupling agents, fluorinated additive agents, rheology control agents, defoaming agents, antistatic agents, anti-fogging agents, adhesion aids, organic pigments, inorganic pigments, extender pigments, organic fillers, and inorganic fillers.

A curable composition containing a calixarene compound according to the present invention has high mold releasability. Thus, the curable composition is particularly useful as a filler resin material but may be used in other applications. For example, the curable composition used as a coating agent or as a paint can form a cured film with high surface smoothness and good antifouling properties.

A curable composition according to the present invention used as a filler resin material can be formed by a known general method. As a relatively new technique among shaping techniques including the use of a forming die, a patterning method will be described below in which an active energy beam curable composition among the curable compositions according to the present invention is used as a nanoimprint lithography resin material.

First, a nanoimprint lithography resin material according to the present invention is applied to a substrate to form an uncured resin film. The thickness of the resin film depends on the shape of the pattern to be formed and preferably ranges from 0.1 to 5 μm. The application method may be any method, such as a spray method, a spin coating method, a dipping method, a roll coating method, a blade coating method, a doctor roll method, a doctor blade method, a curtain coating method, a slit coating method, a bar coating method, a screen printing method, an ink jet printing method, a gravure printing method, or an offset printing method. For a nanoimprint lithography resin material containing an organic solvent, the nanoimprint lithography resin material applied is dried at a temperature in the range of approximately 50° C. to 100° C. for tens of seconds to few minutes to form a resin film.

The substrate may have any shape and may be made of any material, and a pattern can be formed on any desired substrate. The substrate shape may be sheet-like, three-dimensional, plane, or curved. The material of the substrate is, for example, a resin or plastic substrate, such as a cellulose triacetate substrate, a polyester substrate, an acryl substrate, a cycloolefin polymer substrate, a polyamide substrate, a polyimide substrate, a polyethylene substrate, a polypropylene substrate, a polystyrene substrate, a polycarbonate substrate, a poly(phenylene sulfide) (PPS) substrate, an acrylonitrile-butadiene-styrene copolymer resin (ABS) substrate, a sheet molding compound (SMC) substrate, or a bulk molding compound (BMC) substrate; a metal or metallized film substrate, such as nickel, copper, chromium, iron, aluminum, or stainless steel; a transparent electrically conductive film substrate, such as $In_2O_3$—$SnO_2$ (ITO); a semiconductor substrate, such as a silicon substrate, a polysilicon substrate, a silicon carbide substrate, a silicon nitride substrate, a silicon oxide substrate, an amorphous silicon substrate, or a gallium nitride substrate; or quartz, sapphire, glass, ceramic, spin on glass (SOG), or spin on carbon (SOC).

Subsequently, a mold for forming a pattern is pressed on the uncured resin film. The resin material is irradiated with an active energy beam through the mold or substrate to cure the resin material and form a pattern. The material of the mold may be a light-transmitting material, for example, quartz, ultraviolet transmitting glass, sapphire, diamond, a silicone material, such as polydimethylsiloxane, or a transparent resin, such as cycloolefin; or a nontransparent material, such as metal, silicon carbide, or mica. The mold may have any shape and may be planar, belt-like, roll-like, or roll-belt-like.

When the mold is pressed, the resin material may be heated to increase fluidity. The heating temperature is preferably a temperature at which the curing reaction of the resin material does not proceed and preferably ranges from approximately 25° C. to 80° C. when a compound with a (meth)acryloyl group is used as an active energy beam curable resin material.

The active energy beam to be emitted may be any active energy beam that can cure the resin material and that has a wavelength at which the active energy beam can pass through the substrate or mold. In particular, when a compound with a (meth)acryloyl group is used as an active energy beam curable resin material, light with a wavelength of 450 nm or less (an active energy beam, such as ultraviolet light, X-rays, or γ rays can efficiently cause a curing reaction and is preferred.

The application of a pattern formed by a nanoimprint lithography resin material according to the present invention is not particularly limited. The pattern may be used in any application. Due to its high mold releasability, a nanoimprint lithography resin material according to the present invention causes little loss or pattern collapse even in the formation of a fine and complex pattern and can also be suitably used in applications that require high resolution or dimensional control, such as the processing of optical members and integrated circuit (LSI) applications.

EXAMPLES

Although the present invention is more specifically described in the following production examples and examples, the present invention is not limited to these examples. Unless otherwise specified, parts and % in the examples are based on mass.

In the examples, the molecular weight of resin was measured with a gel permeation chromatograph (GPC) under the following conditions.
Measuring apparatus: HLC-8220 manufactured by Tosoh Corporation
Column: guard column $H_{XL}$-H manufactured by Tosoh Corporation
TSKgel G5000HXL manufactured by Tosoh Corporation
TSKgel G4000HXL manufactured by Tosoh Corporation
TSKgel G3000HXL manufactured by Tosoh Corporation
TSKgel G2000HXL manufactured by Tosoh Corporation
Detector: differential refractometer (RI)
Data processing: SC-8010 manufactured by Tosoh Corporation
Measurement conditions: Column temperature 40° C.
Solvent tetrahydrofuran
Flow rate 1.0 ml/min
Reference: polystyrene
Sample: A tetrahydrofuran solution with a resin solid content of 0.4% by mass passed through a microfilter (100 μl).
$^1$H-NMR was measured with "JNM-ECM400S" manufactured by JEOL RESONANCE under the following conditions.
Magnetic field strength: 400 MHz
Number of scans: 16
Solvent: deuterated chloroform
Sample concentration: 2 mg/0.5 ml
$^{13}$C-NMR was measured with "JNM-ECM400S" manufactured by JEOL RESONANCE under the following conditions.
Magnetic field strength: 100 MHz
Number of scans: 1000
Solvent: deuterated chloroform
Sample concentration: 2 mg/0.5 ml
$^{19}$F-NMR was measured with "JNM-ECM400S" manufactured by JEOL RESONANCE under the following conditions.
Magnetic field strength: 400 MHz
Number of scans: 16
Solvent: deuterated chloroform
Sample concentration: 2 mg/0.5 ml
FD-MS was measured with "JMS-T100GC AccuTOF" manufactured by JEOL Ltd. under the following conditions.
Measurement range: m/z=50.00 to 2000.00
Rate of change: 25.6 mA/min
Final current value: 40 mA
Cathode voltage: −10 kV Example 1 Production of Calixarene Compound (1)

<Production of Intermediate (A-1)>

50 g of tert-butyl calix[4]arene represented by the following structural formula (a), 32.26 g of phenol, and 350 ml of anhydrous toluene were charged into a 1-liter four-neck flask equipped with a stirrer, a thermometer, and a reflux condenser tube and were stirred at 300 rpm in a nitrogen flow environment. The tert-butyl calix[4]arene was not dissolved but was suspended. While the flask was placed in an ice bath, 51.37 g of anhydrous aluminum (III) chloride was added in portions. The solution color changed to clear pale orange, and anhydrous aluminum (III) chloride was precipitated on the bottom. After stirring at room temperature for 5 hours, the reaction mixture was transferred into a 1-L beaker, and ice, 100 ml of 1 N hydrochloric acid, and 350 ml of toluene were added to terminate the reaction. The solution color changed to clear light yellow. The reaction mixture was transferred to a separatory funnel, and the organic phase was collected. 100 ml of toluene was added to the aqueous phase to extract organic components. The extraction was performed three times. The extract was mixed with the collected organic phase. The organic phase was dried over anhydrous magnesium sulfate and was then filtered to collect the organic phase. The solvent was evaporated with an evaporator, and a mixture of white crystals and clear colorless liquid was obtained. Methanol was slowly added to the mixture while stirring to reprecipitate the product from the liquid. White crystals were filtered off with a Kiriyama Rohto (funnel), were washed with methanol, and were dried under vacuum. 29.21 g of an intermediate (A-1) represented by the following structural formula (b) was obtained.

[Chem. 16]

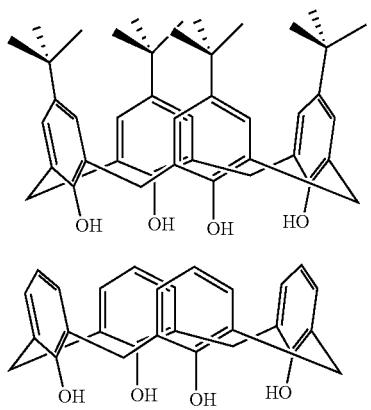

<Allyl Etherification of Intermediate (A-1)>

16.41 g of the intermediate (A-1), 65.64 ml of anhydrous N,N-dimethylformamide, and 37.87 g of 49% aqueous sodium hydroxide were charged into a 1-liter four-neck flask equipped with a stirrer, a thermometer, a dropping funnel, and a reflux condenser tube and were stirred at 300 rpm in a nitrogen flow environment. The solution was clear light yellow. 56.13 g of allyl bromide was added dropwise from a dropping funnel at room temperature for 30 minutes. 30 minutes after the completion of the dropwise addition, a milk white solid was precipitated as slurry. After reaction for another 2 hours, acetic acid and pure water were slowly added to terminate the reaction. Crystals were filtered off with a Kiriyama Rohto (funnel), were washed with methanol, and were then dried under vacuum. 17.94 g of an allyl etherification product of the intermediate (A-1) was obtained.

<Production of Intermediate (B-1)>

14.69 g of the allyl etherification product of the intermediate (A-1) and 58.76 g of N,N-dimethylaniline were charged into a 1-liter four-neck flask equipped with a stirrer, a thermometer, and a reflux condenser tube and were stirred at 300 rpm in a nitrogen flow environment. The mixture was heated to reflux and was stirred for 3 hours. The reaction mixture was cooled to room temperature and was then transferred to a beaker. Ice and 20 g of chloroform were added to the reaction mixture. While the beaker was placed in an ice bath, 48.04 g of 38% concentrated hydrochloric acid was slowly added, and the solution turned to clear light yellow. The reaction mixture was transferred to a separatory funnel, and the organic phase was collected. 20 g of chloroform was added to the aqueous phase to extract organic components. The extraction was performed three times. The extract was mixed with the collected organic phase. The organic phase was dried over anhydrous magnesium sulfate and was then filtered to collect the organic phase. The solvent was evaporated with an evaporator, and a mixture of white crystals and clear light green liquid was obtained. Methanol was slowly added to the mixture to reprecipitate the product from the liquid. White crystals were filtered off with a Kiriyama Rohto (funnel), were washed with methanol, and were dried under vacuum. 12.77 g of an intermediate (B-1) represented by the following structural formula (c) was obtained.

[Chem. 17]

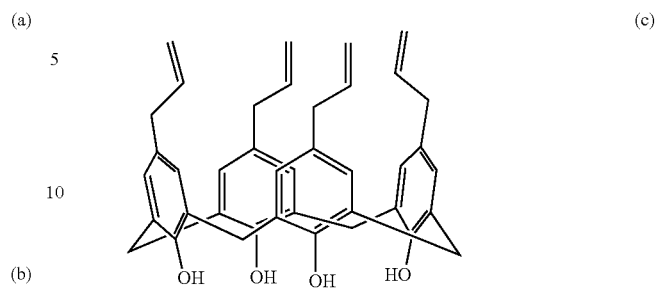

<Introduction of Perfluoroalkyl Group>

10.00 g of the intermediate (B-1), 1.70 g of 2,2'-azobis(2,4-dimethylvaleronitrile) (manufactured by Wako Pure Chemical Industries, Ltd.), 31.5 ml of anhydrous toluene, and 52.02 g of 1,1,2,2-tetrahydroperfluorooctanethiol were charged into a 1-liter four-neck flask equipped with a stirrer, a thermometer, and a reflux condenser tube and were stirred at 300 rpm in a nitrogen flow environment. The mixture was heated to 65° C. and was allowed to react for 12 hours. The reaction mixture was cooled to room temperature and was then transferred to a separatory funnel. 30 g of 1 N aqueous sodium hydrogen carbonate and 30 g of chloroform were added to the reaction mixture to separate the organic phase. 20 g of chloroform was added to the aqueous phase to extract organic components. The extraction was performed three times. The extract was mixed with the collected organic phase. The organic phase was washed with 1 N aqueous sodium hydroxide, was dried over anhydrous magnesium sulfate, and was filtered. The solvent was evaporated with an evaporator. The resulting clear red liquid was cooled with ice, and methanol was added to the liquid to reprecipitate crystals. Gray crystals were filtered off with a Kiriyama Rohto (funnel), were washed with methanol, and were dried under vacuum. 31.08 g of a calixarene compound (1) represented by the following structural formula (d) was obtained.

[Chem. 18]

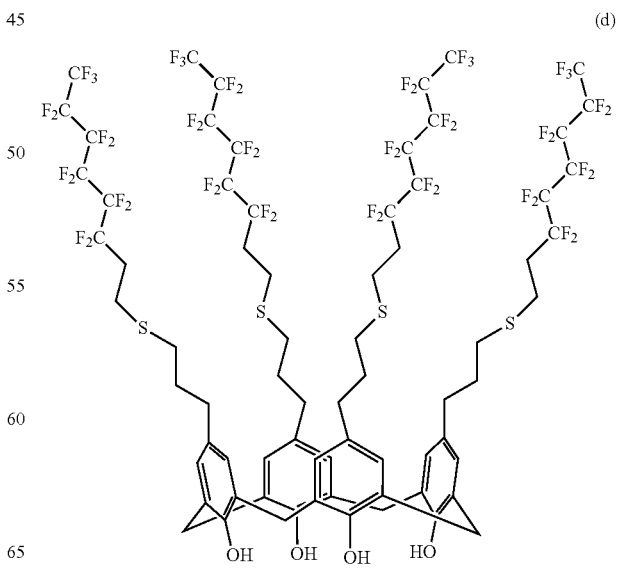

Example 2 Production of Calixarene Compound (2)

10.00 g (4.750 mmol) of the calixarene compound (1) produced in Example 1, 55.00 g (947.0 mmol) of anhydrous acetone, 7.88 g (57.00 mmol) of potassium carbonate, and 8.72 g (57.02 mmol) of methyl 2-bromoacetate were charged into a 300-milliliter four-neck flask equipped with a stirrer, a thermometer, and a reflux condenser tube and were heated under reflux for 60 hours. The mixture was cooled to room temperature, and ion-exchanged water and 1 N hydrochloric acid were added to pH 6. 50 g of chloroform was added to the reaction mixture. The reaction mixture was transferred to a separatory funnel to separate the organic phase. The aqueous phase was then extracted with 50 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent: n-hexane:acetone=3:1). A clear orange liquid was obtained. The solvent was concentrated, and chloroform/methanol was added for reprecipitation. An ochreous solid was filtered off through a Kiriyama Rohto (funnel) and was dried under vacuum (at 60° C. for 6 hours or more). 9.84 g of a calixarene compound (2) represented by the following structural formula (e) was obtained. The yield was 86.5%.

[Chem. 19]

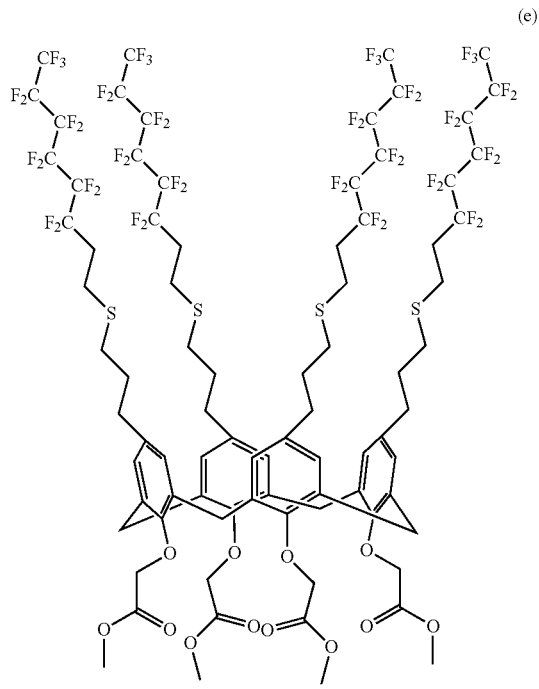

(e)

Example 3 Production of Calixarene Compound (3)

A 500-milliliter four-neck flask equipped with a stirrer, a thermometer, and a reflux condenser tube was charged with 8.00 g (110.94 mmol) of tetrahydrofuran and was placed in an ice bath. 0.507 g (13.36 mmol) of lithium aluminum hydride was slowly added to the tetrahydrofuran. 4.00 g (1.6711 mmol) of the calixarene compound (2) dissolved in 32.00 g (443.77 mmol) of tetrahydrofuran was slowly added from a dropping funnel at 5° C. or less. Gray suspension. The mixture was allowed to react at room temperature for 6 hours. In an ice bath, 2 g of ion-exchanged water, 5 g of 1 N hydrochloric acid, 20 g of ion-exchanged water, and 30 g of chloroform were added. The reaction liquid was filtered through diatomaceous earth. 30 g of chloroform was added to the filtrate. The reaction mixture was transferred to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent:n-hexane:acetone=3:1). A clear light yellow liquid was obtained. The solvent was concentrated, and chloroform/methanol was added for reprecipitation. White solid was filtered off through a Kiriyama Rohto (funnel) and was dried under vacuum (at 60° C. for 6 hours or more). 2.978 g of a calixarene compound (3) represented by the following structural formula (f) was obtained. The yield was 78.1%.

[Chem. 20]

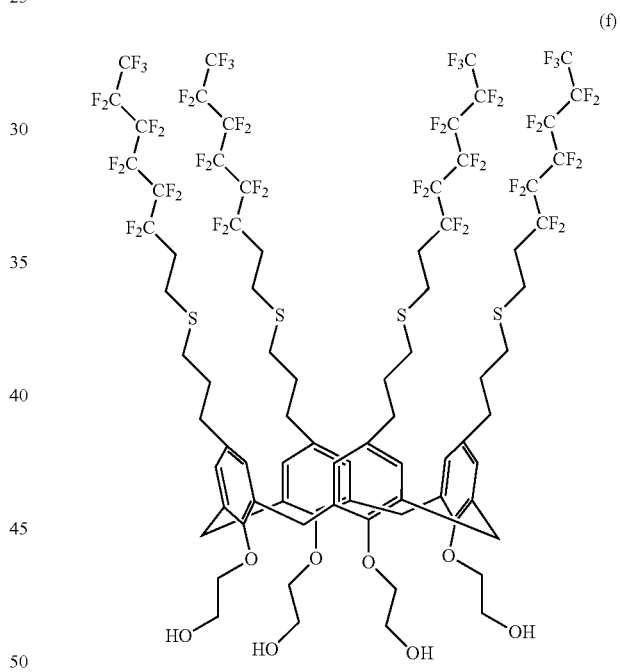

(f)

Example 4 Production of Calixarene Compound (4)

2.00 g (0.9499 mmol) of the calixarene compound (1), 20.55 g (285.0 mmol) of anhydrous THF, 1.96 g (49.40 mmol) of 60% NaH, and 30.48 g (120.0 mmol) of N-(2-bromoethyl)phthalimide were quickly charged into a 200-milliliter four-neck flask equipped with a stirrer, a thermometer, a dropping funnel, and a reflux condenser tube and were stirred at 300 rpm under a nitrogen flow at room temperature. A light yellow suspension was obtained. The light yellow suspension was heated and refluxed for 12 hours. Methanol was slowly added to quench the reaction. The solution was evaporated, and 50 g of chloroform and 1 N HCl were added to pH 3 to separate the organic phase. The aqueous phase was then extracted with 20 g of chloroform three times and was mixed with the organic phase. After washing with 1 M aqueous Na2CO3 and ion-exchanged water, the organic phase was predried over anhydrous magnesium sulfate and was filtered. The solvent was evaporated with an evaporator, and in an ice bath methanol was added for reprecipitation. A milk white solid was filtered off through a Kiriyama Rohto (funnel) and was washed with methanol. The milk white solid was dried under vacuum (at 60° C. for 12 hours or more), and 1.2864 g of a calixarene compound (4) represented by the following structural formula (g) was obtained. The yield was 48.4%.

[Chem. 21]

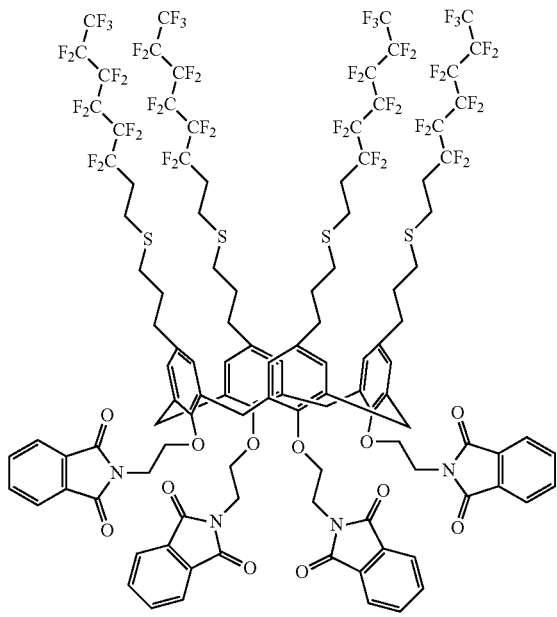

(g)

Example 5 Production of Calixarene Compound (5)

1.2864 g (0.4597 mmol) of the calixarene compound (4), 15.42 g (334.70 mmol) of ethanol, and 0.4845 g (0.9195 mmol) of 95% hydrazine monohydrate were quickly charged into a 100-milliliter four-neck flask equipped with a stirrer, a thermometer, a dropping funnel, and a reflux condenser tube and were heated under reflux for 5 hours under a nitrogen flow at 300 rpm. A light yellow suspension was obtained. After cooling, the solution was evaporated, and 20 g of chloroform and 20 g of ion-exchanged water were added to separate the organic phase. The aqueous phase was then extracted with 20 g of chloroform three times and was mixed with the organic phase. The organic phase was predried over anhydrous magnesium sulfate and was filtered. The solvent was evaporated with an evaporator. 7.00 g (218.5 mmol) of methanol and 0.3644 g (3.698 mmol) of 37% concentrated hydrochloric acid were then charged and were heated under reflux under a nitrogen flow for 4 hours. The reaction mixture was cooled to room temperature and was then transferred to a separatory funnel. 20 g of ion-exchanged water and 20 g of chloroform were added to the reaction mixture to separate the organic phase. The aqueous phase was then extracted with 20 g of chloroform three times and was mixed with the organic phase. After washing with saturated saline, the organic phase was predried over anhydrous magnesium sulfate and was filtered. The solvent was evaporated with an evaporator, and a red viscous liquid was subjected to column chromatography (developing solvent: n-hexane:acetone=3:1). A clear light blue liquid was obtained. The solvent was concentrated, and chloroform/methanol was added for reprecipitation. Gray solid was filtered off through a Kiriyama Rohto (funnel) and was dried under vacuum (at 60° C. for 6 hours or more). 0.3664 g of a calixarene compound (5) represented by the following structural formula (h) was obtained. The yield was 35.0%.

[Chem. 22]

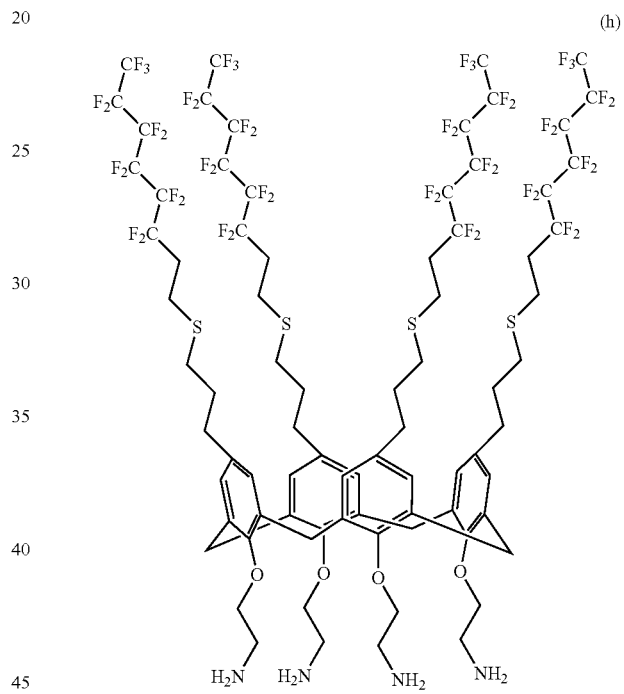

(h)

Example 6 Production of Calixarene Compound (6)

4.00 g (1.671 mmol) of the calixarene compound (2), 30.00 g (416.05 mmol) of tetrahydrofuran, 26.00 g (564.4 mmol) of ethanol, and 1.24 g (22.11 mmol) of potassium hydroxide were charged into a 500-milliliter four-neck flask equipped with a stirrer, a thermometer, and a reflux condenser tube and were heated under reflux for 6 hours. White suspension. After cooling to room temperature, ion-exchanged water and chloroform were added, and the flask was placed in an ice bath. 5 N hydrochloric acid was then slowly added to pH 1. The reaction mixture was transferred with 50 g of chloroform to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and a milk white solid was obtained. The milk white solid was dried under vacuum (at 60° C. for 12 hours or more), and 3.883 g of a calixarene compound (6) represented by the following structural formula (I) was obtained. The yield was 99.4%.

[Chem. 23]

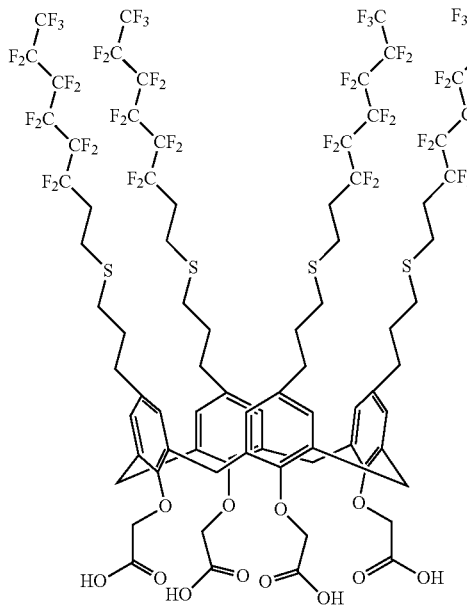

(i)

Example 7 Production of Calixarene Compound (7)

5.00 g (2.416 mmol) of the calixarene compound (1), 17.66 g (241.6 mmol) of anhydrous N,N-dimethylformamide, and 1.16 g (29.00 mmol) of 50% aqueous NaOH were quickly charged into a 100-milliliter four-neck flask equipped with a stirrer, a thermometer, a dropping funnel, and a reflux condenser tube and were stirred at 300 rpm under a nitrogen flow at 65° C. A clear light yellow solution was obtained. 4.38 g (29.00 mmol) of allyl bromide was then added dropwise from a dropping funnel for 30 minutes. 30 minutes after the completion of the addition, a milk white solid was precipitated as slurry. After that, the reaction occurred for 10 hours. Acetic acid and ion-exchanged water were slowly added to quench the reaction. A solid precipitated was filtered through a Kiriyama Rohto (funnel) and was washed with methanol. The resulting pink solid was dried under vacuum (at 60° C. for 12 hours or more), and 4.029 g of a calixarene compound (7) represented by the following structural formula (j) was obtained. The yield was 73.6%.

[Chem. 24]

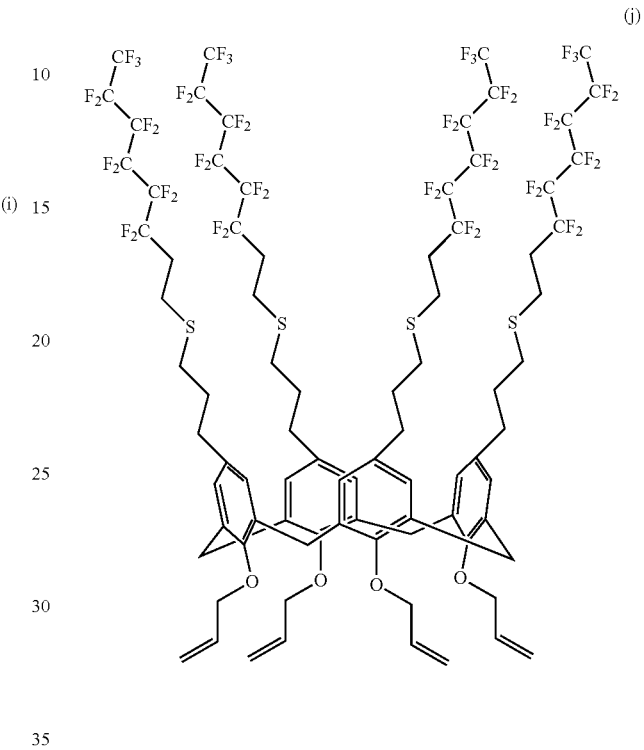

(j)

Example 8 Production of Calixarene Compound (8)

1.500 g (0.6621 mmol) of the calixarene compound (7), 6.01 g (66.21 mmol) of anhydrous toluene, 0.0658 g (0.2649 mmol) of 2,2'-azobis(2,4-dimethylvaleronitrile) (manufactured by Wako Pure Chemical Industries, Ltd.), and 0.4031 g (0.5296 mmol) of thioacetic acid were charged into a 200-milliliter four-neck flask equipped with a stirrer, a thermometer, a dropping funnel, and a reflux condenser tube and were stirred at 300 rpm under a nitrogen flow for 12 hours at 65° C. The reaction mixture was cooled to room temperature and was then transferred to a separatory funnel. 15 g of 1 N aqueous NaHCO$_3$ and 15 g of chloroform were added to the reaction mixture to separate the organic phase. The aqueous phase was then extracted with 15 g of chloroform three times and was mixed with the organic phase. After separation with 15 g of 1 N aqueous NaOH, the organic phase was predried over anhydrous magnesium sulfate and was filtered. The solvent was evaporated with an evaporator, and a clear red liquid was obtained. In an ice bath, methanol was added for reprecipitation. A milk white solid was filtered off through a Kiriyama Rohto (funnel) and was washed with methanol. The milk white solid was dried under vacuum (at 60° C. for 12 hours or more), and 1.543 g of a calixarene compound (8) represented by the following structural formula (k) was obtained. The yield was 90.7%.

[Chem. 25]

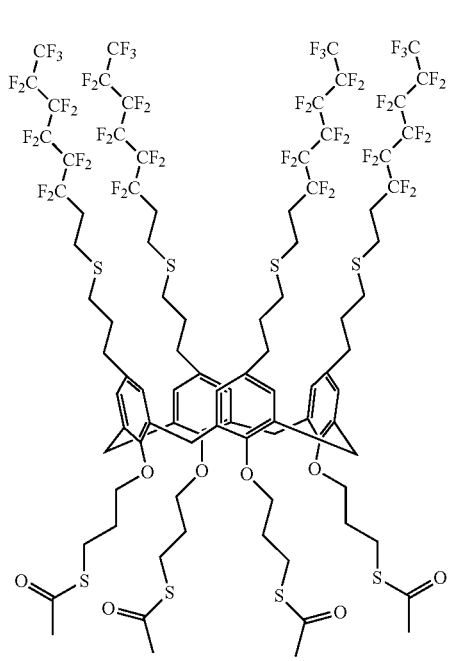

(k)

[Chem. 26]

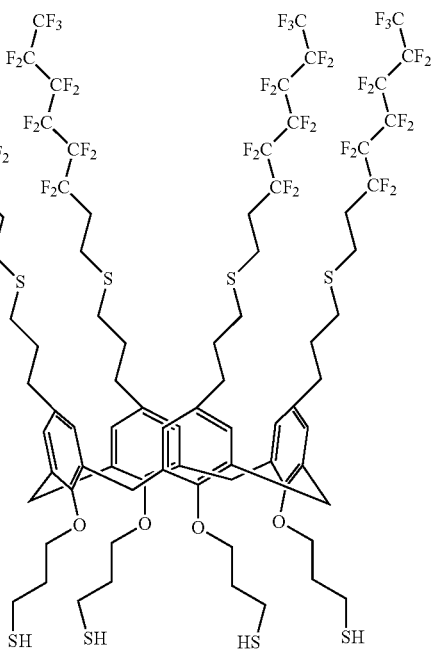

(l)

Example 9 Production of Calixarene Compound (9)

1.543 g (0.6004 mmol) of the calixarene compound (8), 2.00 g (27.74 mmol) of THF, 4.00 g (124.84 mmol) of methanol, and 0.9754 g (9.900 mmol) of 37% concentrated hydrochloric acid were charged into a 100-milliliter four-neck flask equipped with a stirrer, a thermometer, and a reflux condenser tube and were stirred at 300 rpm under a nitrogen flow for 8 hours at 65° C. The reaction mixture was cooled to room temperature and was then transferred to a separatory funnel. 20 g of ion-exchanged water and 20 g of chloroform were added to the reaction mixture to separate the organic phase. The aqueous phase was then extracted with 20 g of chloroform three times and was mixed with the organic phase. After washing with 15 g of saturated aqueous NaHCO₃ and then with saturated saline, the organic phase was predried over anhydrous magnesium sulfate and was filtered. The solvent was evaporated with an evaporator, and a clear red liquid was obtained. In an ice bath, normal hexane and methanol were added for reprecipitation. A milk white solid was filtered off through a Kiriyama Rohto (funnel) and was washed with methanol. The milk white solid was dried under vacuum (at 60° C. for 12 hours or more), and 1.084 g of a calixarene compound (9) represented by the following structural formula (1) was obtained. The yield was 75.2%.

Example 10 Production of Calixarene Compound (10)

1.500 g (0.7248 mmol) of the calixarene compound (1), 15.68 g (217.45 mmol) of anhydrous THF, 0.3479 g (8.698 mmol) of 60% NaH, and 2.3755 g (8.698 mmol) of diethyl 2-bromobutylphosphonate were quickly charged into a 100-milliliter four-neck flask equipped with a stirrer, a thermometer, a dropping funnel, and a reflux condenser tube and were stirred at 300 rpm under a nitrogen flow at room temperature. A light yellow suspension was obtained. The light yellow suspension was heated and refluxed for 12 hours. Methanol was slowly added to quench the reaction. The solution was evaporated, and 50 g of chloroform and 25 g of 1 N HCl were added to separate the organic phase. The aqueous phase was then extracted with 20 g of chloroform three times and was mixed with the organic phase. After washing with ion-exchanged water, the organic phase was predried over anhydrous magnesium sulfate and was filtered. The solvent was evaporated with an evaporator, and a red viscous liquid was subjected to column chromatography (developing solvent:n-hexane:acetone=3:1). A clear orange liquid was obtained. The solvent was concentrated, and chloroform/methanol was added for reprecipitation. An ochreous solid was filtered off through a Kiriyama Rohto (funnel) and was dried under vacuum (at 60° C. for 6 hours or more). 1.078 g of a calixarene compound (10) represented by the following structural formula (m) was obtained. The yield was 52.4%.

[Chem. 27]

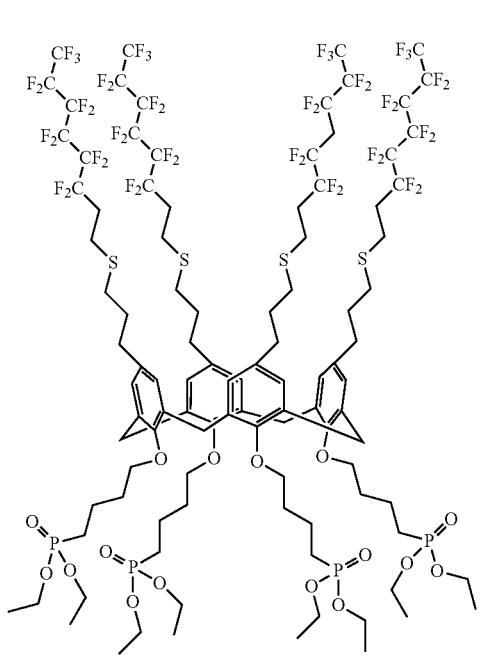

(m)

Example 11 Production of Calixarene Compound (11)

1.078 g (0.8258 mmol) of the calixarene compound (10), 8.00 g (194.9 mmol) of anhydrous acetonitrile, and 2.086 g (13.63 mmol) of trimethylsilyl bromide were quickly charged into a 100-milliliter four-neck flask equipped with a stirrer, a thermometer, a dropping funnel, and a reflux condenser tube and were heated under reflux under a nitrogen flow at 300 rpm for 6 hours. A light yellow suspension was obtained. 5.00 g (156.0 mmol) of methanol was added to the light yellow suspension, and the light yellow suspension was heated under reflux for another 2 hours. After cooling, the solution was evaporated, and 20 g of chloroform and 20 g of ion-exchanged water were added to separate the organic phase. The aqueous phase was then extracted with 10 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent: n-hexane:acetone=3:1). A clear yellow liquid was obtained. The solvent was concentrated, and chloroform/methanol was added for reprecipitation. An ochreous solid was filtered off through a Kiriyama Rohto (funnel) and was dried under vacuum (at 60° C. for 6 hours or more). 1.399 g of a calixarene compound (11) represented by the following structural formula (n) was obtained. The yield was 64.8%.

[Chem. 28]

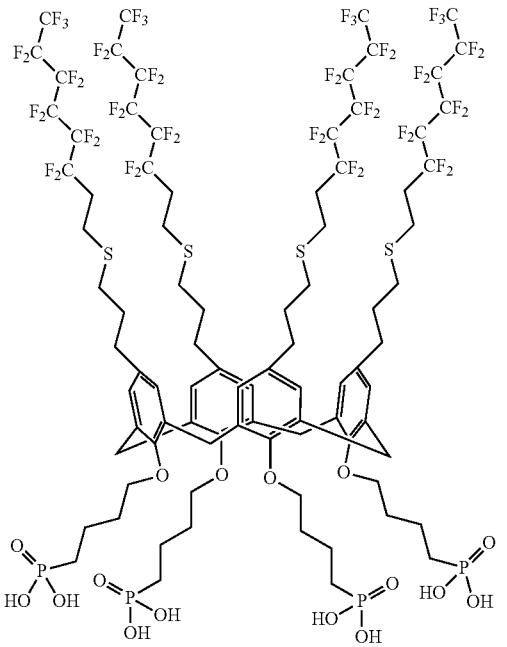

(n)

Example 12 Production of Calixarene Compound (12)

In a 100-milliliter four-neck flask equipped with a stirrer, a thermometer, a dropping funnel, and a reflux condenser tube, 1.00 g (0.4383 mmol) of the calixarene compound (3) was dissolved in 8.00 g (94.20 mmol) of anhydrous dichloromethane, and 1.7677 g (17.470 mmol) of anhydrous triethylamine was added. In an ice bath, 1.6808 g (4.4306 mmol) of bis(2,2,2-trichloroethyl) phosphorochloridate was then added and was allowed to react at room temperature for 12 hours. 20 g of dichloromethane and 20 g of saturated aqueous NaHCO$_3$ were added to separate the organic phase. The aqueous phase was then extracted with 20 g of dichloromethane three times and was mixed with the organic phase. The organic phase was washed with saturated saline, was predried over anhydrous magnesium sulfate, and was filtered. The residue was dissolved in pyridine:acetic acid=5:1, was held at 0° C., and 6 g of activated zinc was added. The reaction mixture was stirred at room temperature overnight. A solid was filtered off, and the solvent was removed. The reaction liquid was then filtered through diatomaceous earth, was treated with 5 N aqueous sodium hydroxide, and was washed with dichloromethane. The aqueous layer was treated with 2 N hydrochloric acid to form a precipitate. The precipitate was washed with 0.1 N hydrochloric acid, and a white solid was obtained. The white solid was dried under vacuum (at 60° C. for 6 hours or more), and 0.2486 g of a calixarene compound (12) represented by the following structural formula (o) was obtained. The yield was 21.8%.

[Chem. 29]

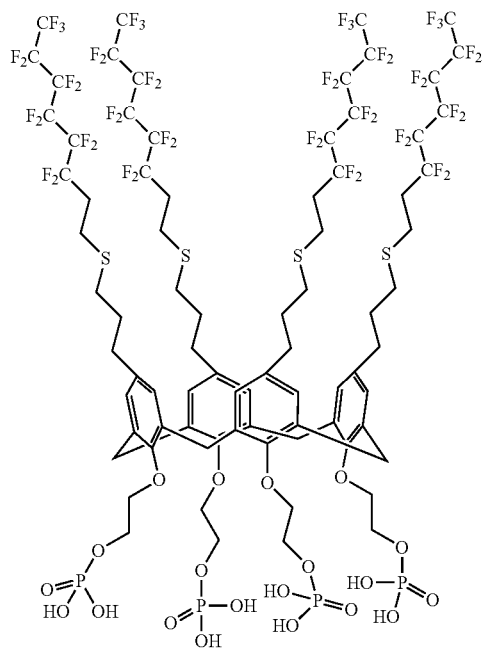

(o)

[Chem. 30]

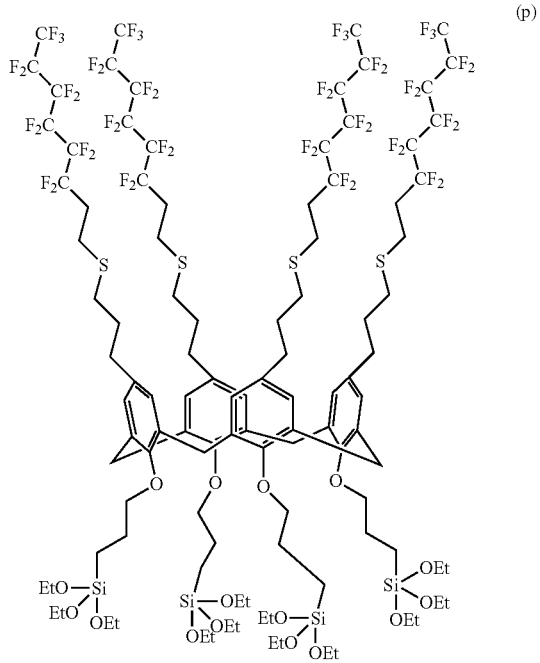

(p)

Example 13 Production of Calixarene Compound (13)

1.00 g (0.4414 mmol) of the calixarene compound (3), 2.078 g (22.07 mmol) of anhydrous toluene, and 0.00127 g (0.0033 mmol) of a 1,3-divinyl-1,1,3,3-tetramethyldisiloxane platinum (0) complex xylene solution were quickly charged into a 30-milliliter four-neck flask equipped with a stirrer, a thermometer, a dropping funnel, and a reflux condenser tube and were stirred at 300 rpm for 30 minutes under a nitrogen flow in an ice bath. 0.8701 g (5.296 mmol) of triethoxysilane was then added dropwise with a syringe for 30 minutes. The mixture was heated to 50° C. in 30 minutes after the completion of the dropwise addition and was allowed to react for 8 hours. The solution turned to a clear light yellow solution. After cooling, the platinum complex was filtered off through activated carbon and diatomaceous earth, and the filtrate was concentrated to produce a clear light yellow oil. The oil was subjected to column chromatography (developing solvent:n-hexane:acetone=3:1). A clear orange liquid was obtained. The solvent was concentrated, and a clear light yellow oil was obtained. The clear light yellow oil was dried under vacuum (at 60° C. for 6 hours or more), and 0.4244 g of a calixarene compound (13) represented by the following structural formula (p) was obtained. The yield was 32.9%.

Example 14 Production of Calixarene Compound (14)

1.000 g (0.4278 mmol) of the calixarene compound (6), 0.03160 g (0.0856 mmol) of tetrabutylammonium iodide, 7.711 g (85.56 mmol) of 1-methoxy-2-propanol, 0.003 g (0.0171 mmol) of phenothiazine, and 0.5140 g (5.133 mmol) of vinyl glycidyl ether were stirred in a 50-milliliter four-neck flask equipped with a stirrer, a thermometer, and a reflux condenser tube. The mixture was heated at 90° C. for 20 hours with oxygen bubbling. A clear brown solution. The mixed solution was cooled to room temperature and was transferred to a beaker. 1 N hydrochloric acid and 30 g of chloroform were added. The reaction mixture was transferred to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent:n-hexane:acetone=95:5). A clear light yellow liquid was obtained. The solvent was concentrated, the solvent was concentrated, and a clear light yellow oil was obtained. The clear light yellow oil was dried under vacuum (at 60° C. for 6 hours or more), and 0.3537 g of a calixarene compound (14) represented by the following structural formula (q) was obtained. The yield was 30.2%.

[Chem. 31]

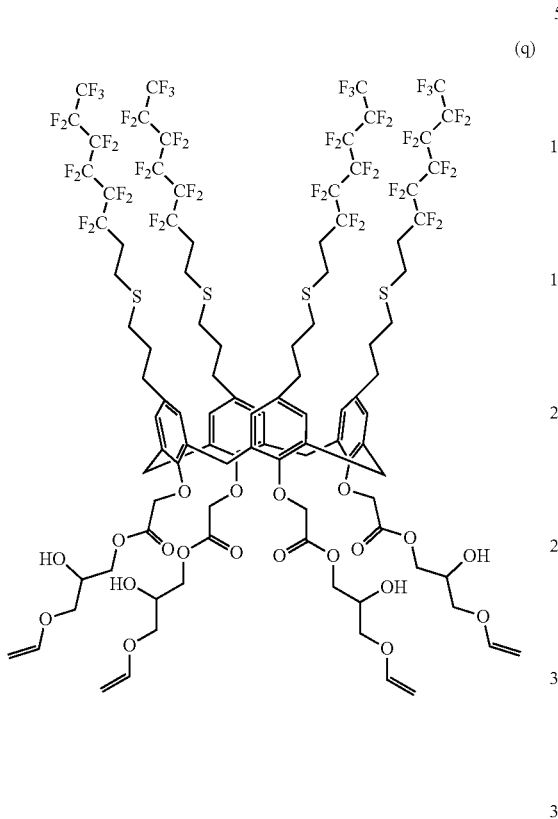

(q)

[Chem. 32]

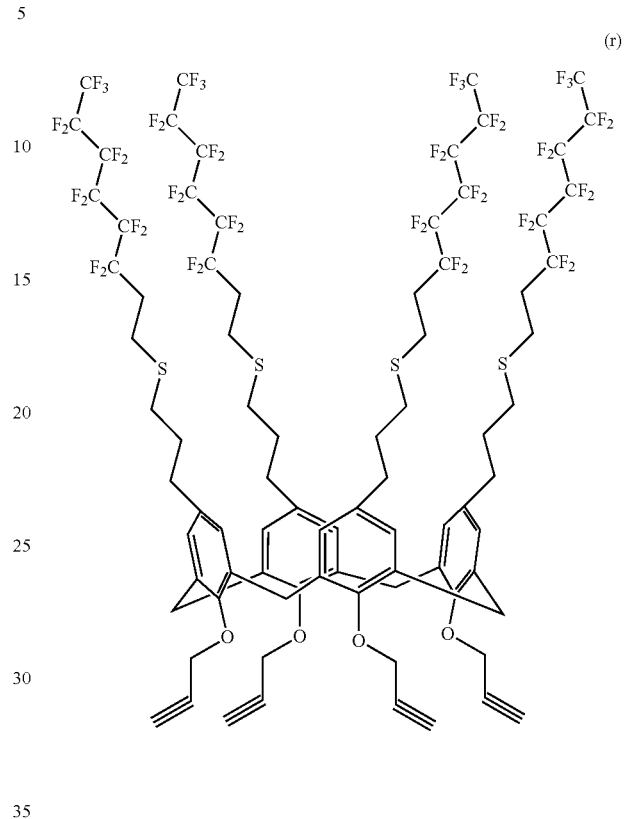

(r)

Example 15 Production of Calixarene Compound (15)

1.00 g (0.4832 mmol) of the calixarene compound (1) and 3.53 g (48.32 mmol) of anhydrous N,N-dimethylformamide were charged into a 50-milliliter four-neck flask equipped with a stirrer, a thermometer, a dropping funnel, and a reflux condenser tube, and 0.0928 g (3.866 mmol) of 60% NaH was added in small amounts in an ice bath. When the solution color changed while stirring, 0.5748 g (3.866 mmol) of propargyl bromide (80% in toluene, approximately 9.2 mol/L) was added. The solution was stirred at room temperature for 5 hours. A brown suspension solution. Ion-exchanged water was slowly added to quench the reaction. 1 N hydrochloric acid was then added to pH 3.30 g of chloroform was added to the reaction mixture. The reaction mixture was transferred to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and chloroform/methanol was added for reprecipitation. A gray solid was filtered off through a Kiriyama Rohto (funnel) and was dried under vacuum (at 60° C. for 6 hours or more). 0.7265 g of a calixarene compound (15) represented by the following structural formula (r) was obtained. The yield was 66.6%.

Example 16 Production of Calixarene Compound (16)

2.00 g (0.9664 mmol) of the calixarene compound (1), 14.00 g (194.2 mmol) of tetrahydrofuran, 0.76 g (2.900 mmol) of triphenylphosphine, and 0.3773 g (2.899 mmol) of hydroxyethyl methacrylate were stirred in a 100-milliliter four-neck flask equipped with a stirrer, a thermometer, and a reflux condenser tube. A clear light yellow solution. In an ice bath, 0.5863 g (2.899 mmol) of diisopropyl azodicarboxylate was then added dropwise for 30 minutes. A clear orange solution. The solution was stirred at room temperature for 6 hours. Hexane was added to the reaction solution. By-products, such as triphenylphosphine, were removed by precipitation. The reaction solution was extracted with chloroform, was washed with water and saturated saline, and was dried over magnesium sulfate. The solvent was evaporated with an evaporator, and a red viscous liquid was subjected to column chromatography (developing solvent: n-hexane:acetone=95:5). A clear light yellow liquid was obtained. The solvent was concentrated, and chloroform/methanol was added for reprecipitation. White crystals were filtered off through a Kiriyama Rohto (funnel) and were dried under vacuum (at 60° C. for 6 hours or more). 1.33 g of a calixarene compound (16) represented by the following structural formula (s) was obtained. The yield was 60.0%.

[Chem. 33]

(s)

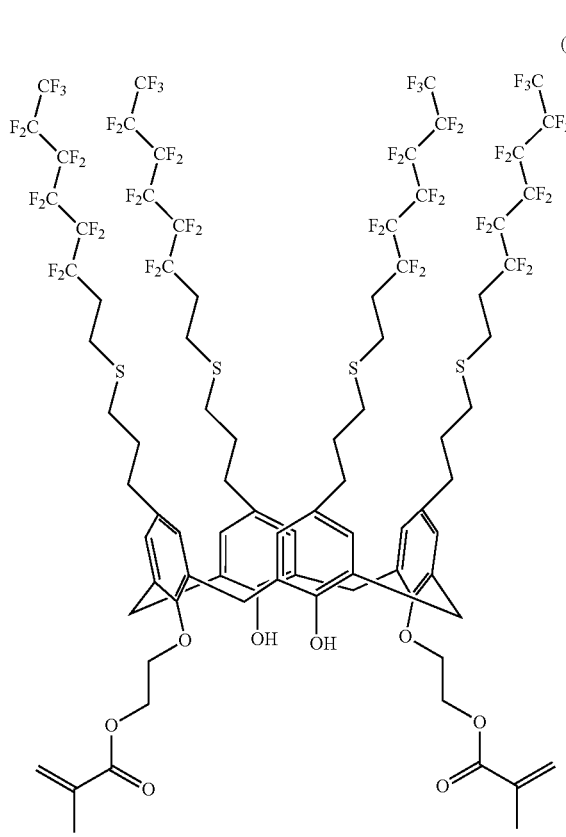

[Chem. 34]

(t)

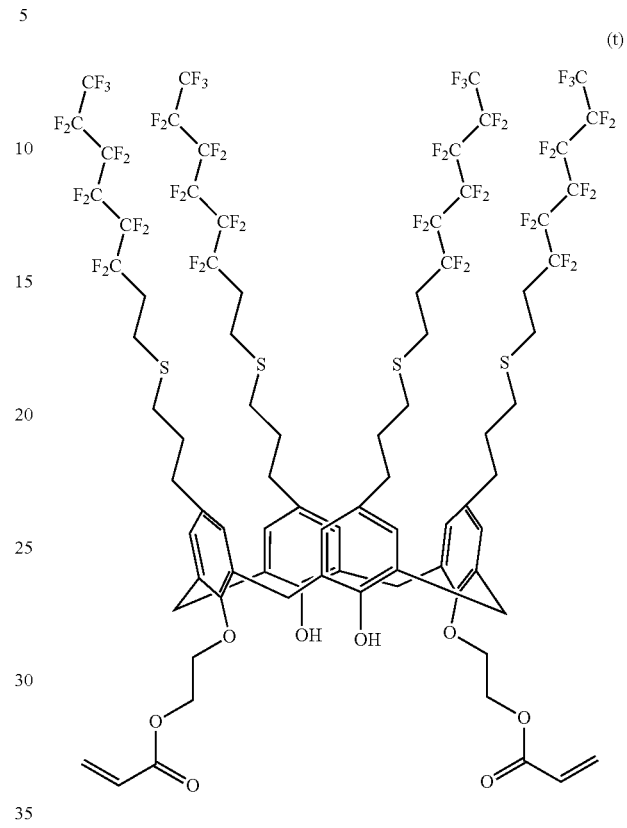

Example 17 Production of Calixarene Compound (17)

2.00 g (0.9664 mmol) of the calixarene compound (1), 14.00 g (194.2 mmol) of tetrahydrofuran, 0.76 g (2.900 mmol) of triphenylphosphine, and 0.3367 g (2.899 mmol) of β-hydroxyethyl acrylate were stirred in a 100-milliliter four-neck flask equipped with a stirrer, a thermometer, and a reflux condenser tube. A clear light yellow solution. In an ice bath, 0.5863 g (2.899 mmol) of diisopropyl azodicarboxylate was then added dropwise for 30 minutes. A clear orange solution. The solution was stirred at room temperature for 6 hours. Hexane was added to the reaction solution. By-products, such as triphenylphosphine, were removed by precipitation. The reaction solution was extracted with chloroform, was washed with water and saturated saline, and was dried over magnesium sulfate. The solvent was evaporated with an evaporator, and a red viscous liquid was subjected to column chromatography (developing solvent: n-hexane:acetone=95:5). A clear light yellow liquid was obtained. The solvent was concentrated, and chloroform/methanol was added for reprecipitation. White crystals were filtered off through a Kiriyama Rohto (funnel) and were dried under vacuum (at 60° C. for 6 hours or more). 1.2590 g of a calixarene compound (17) represented by the following structural formula (t) was obtained. The yield was 57.5%.

Example 18 Production of Calixarene Compound (18)

2.00 g (0.8906 mmol) of the calixarene compound (3), 13.00 g (180.3 mmol) of tetrahydrofuran, 1.4016 g (5.343 mmol) of triphenylphosphine, and 0.3851 g (5.344 mmol) of acrylic acid were stirred in a 200-milliliter four-neck flask equipped with a stirrer, a thermometer, and a reflux condenser tube. A clear light yellow solution. In an ice bath, 1.0805 g (5.344 mmol) of diisopropyl azodicarboxylate was then added dropwise for 30 minutes. A clear red solution. The solution was stirred at room temperature for 6 hours. Hexane was added to the reaction solution. By-products, such as triphenylphosphine, were removed by precipitation. The reaction solution was extracted with chloroform, was washed with water and saturated saline, and was dried over magnesium sulfate. The solvent was evaporated with an evaporator, and a red viscous liquid was subjected to column chromatography (developing solvent:n-hexane:acetone=95:5). A clear light yellow liquid was obtained. The solvent was concentrated, and chloroform/methanol was added for reprecipitation. White crystals were filtered off with a Kiriyama Rohto (funnel) and were dried under vacuum (at 60° C. for 6 hours or more). 1.3418 g of a calixarene compound (18) represented by the following structural formula (u) was obtained. The yield was 61.2%.

[Chem. 35]

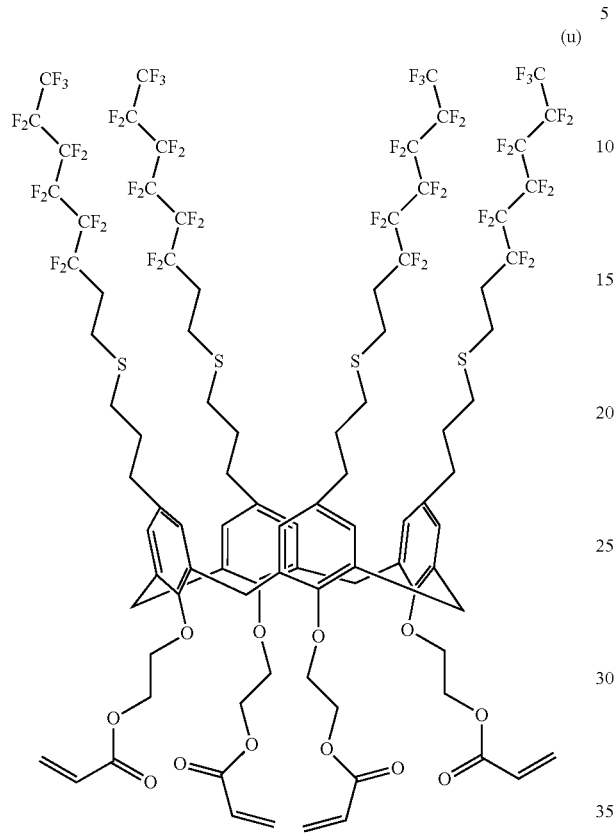

(u)

Example 19 Production of Calixarene Compound (19)

1.000 g (0.4278 mmol) of the calixarene compound (6), 0.03160 g (0.0856 mmol) of tetrabutylammonium iodide, 7.711 g (85.56 mmol) of 1-methoxy-2-propanol, 0.003 g (0.0171 mmol) of phenothiazine, and 0.7300 g (5.133 mmol) of GMA were stirred in a 300-milliliter four-neck flask equipped with a stirrer, a thermometer, and a reflux condenser tube. The mixture was heated at 90° C. for 20 hours with oxygen bubbling. A clear brown solution. The mixed solution was cooled to room temperature and was transferred to a beaker. 1 N hydrochloric acid and 30 g of chloroform were added. The reaction mixture was transferred to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent:n-hexane:acetone=95:5). A clear light yellow liquid was obtained. The solvent was concentrated, and chloroform/methanol was added for reprecipitation. A white solid was filtered off through a Kiriyama Rohto (funnel) and was dried under vacuum (at 60° C. for 6 hours or more). 0.5483 g of a calixarene compound (19) represented by the following structural formula (v) was obtained. The yield was 44.1%.

[Chem. 36]

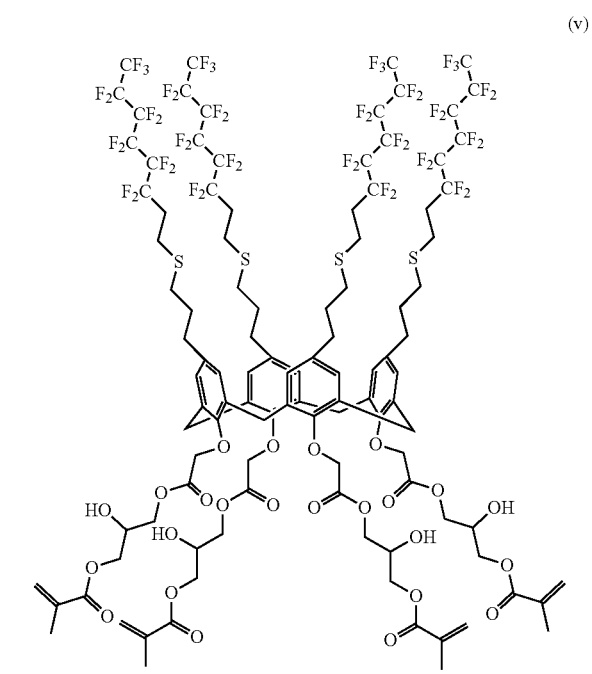

(v)

Example 20 Production of Calixarene Compound (20)

1.000 g (0.4453 mmol) of the calixarene compound (3), 5.00 g (50.44 mmol) of N-methylpyrrolidone, 0.3771 g (2.672 mmol) of 2-acryloyloxyethyl isocyanate, 0.001 g (0.005018 mmol) of phenothiazine, and 0.001 g (0.001583 mmol) of dibutyltin dilaurate were stirred in a 100-milliliter four-neck flask equipped with a stirrer, a thermometer, and a reflux condenser tube. The mixture was heated at 780° C. for 10 hours with oxygen bubbling. A clear brown solution. The reaction solution was cooled to room temperature and was slowly added dropwise to 300 g of ion-exchanged water while stirring to precipitate a solid. Chloroform/methanol was added for reprecipitation. White crystals were filtered off with a Kiriyama Rohto (funnel) and were dried under vacuum (at 60° C. for 6 hours or more). 0.3929 g of a calixarene compound (20) represented by the following structural formula (w) was obtained. The yield was 31.4%.

[Chem. 37]

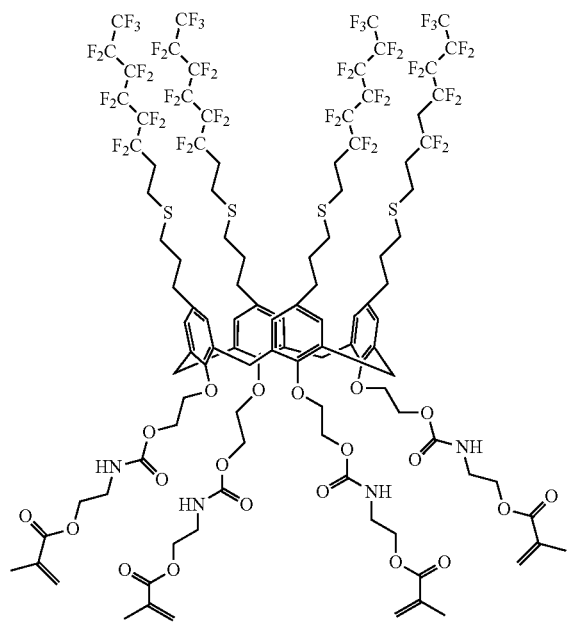

(w)

[Chem. 38]

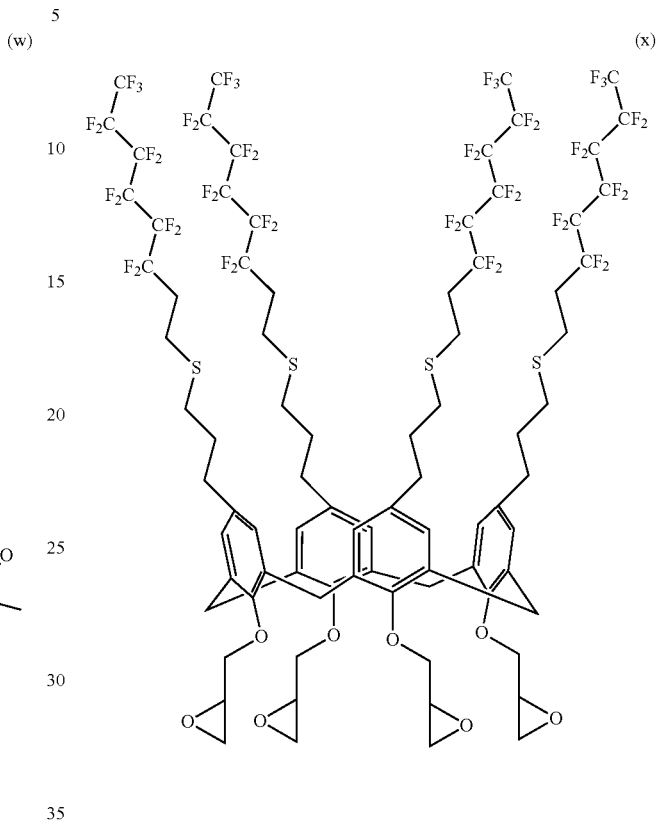

(x)

Example 21 Production of Calixarene Compound (21)

In a 100-milliliter four-neck flask equipped with a stirrer, a thermometer, and a reflux condenser tube, 1.000 g (0.4414 mmol) of the calixarene compound (7) was dissolved in 7.50 g (88.27 mmol) of dichloromethane. 0.2225 g (2.648 mmol) of sodium hydrogen carbonate was then added, and 0.516 g (1.942 mmol) of m-chloroperbenzoic acid was then added in small amounts. The solution was stirred at room temperature for 7 days. A cream suspension. The reaction mixture was washed with saturated aqueous sodium hydrogen carbonate. 20 g of dichloromethane was added to the reaction mixture. The reaction mixture was transferred to a separatory funnel to separate the organic phase. The aqueous phase was then extracted with 20 g of dichloromethane three times and was mixed with the organic phase. The organic phase was washed with 10% aqueous sodium thiosulfate. The organic phase was predried over anhydrous magnesium sulfate and was filtered. The solvent was evaporated with an evaporator, and a yellow viscous liquid was subjected to column chromatography (developing solvent:n-hexane:acetone=90:10). A clear light yellow liquid was obtained. The solvent was concentrated, and chloroform/methanol was added for reprecipitation. An orange solid was filtered off with a Kiriyama Rohto (funnel) and was dried under vacuum (at 60° C. for 6 hours or more). 0.5281 g of a calixarene compound (21) represented by the following structural formula (x) was obtained. The yield was 51.7%.

Example 22 Production of Calixarene Compound (22)

1.000 g (0.4832 mmol) of the calixarene compound (1), 0.0357 g (0.09664 mmol) of tetrabutylammonium iodide, 10.00 g (100.87 mmol) of N-methylpyrrolidone, 0.7838 g (2.899 mmol) of (3-ethyl-3-oxetanyl)methyl p-toluenesulfonate, and 0.1627 g (2.899 mmol) of potassium hydroxide were stirred in a 50-milliliter four-neck flask equipped with a stirrer, a thermometer, and a reflux condenser tube. The mixture was heated at 80° C. for 20 hours. A clear brown solution. The mixed solution was cooled to room temperature and was transferred to a beaker. 1 N hydrochloric acid and 30 g of chloroform were added. The reaction mixture was transferred to a separatory funnel to separate the organic phase. The aqueous phase was then extracted with 30 g of chloroform three times and was mixed with the organic phase. The organic phase was predried over anhydrous magnesium sulfate and was filtered. The solvent was evaporated with an evaporator, and a red viscous liquid was subjected to column chromatography (developing solvent: n-hexane:acetone=95:5). A clear light yellow liquid was obtained. The solvent was concentrated, and chloroform/methanol was added for reprecipitation. An orange solid was filtered off through a Kiriyama Rohto (funnel) and was dried under vacuum (at 60° C. for 6 hours or more). 0.5282 g of a calixarene compound (22) represented by the following structural formula (y) was obtained. The yield was 44.4%

[Chem. 39]

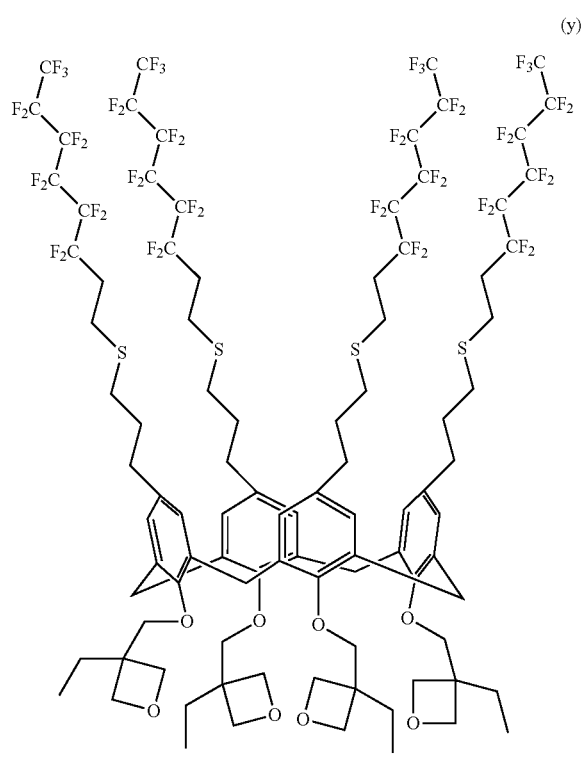

(y)

Example 23 Production of Calixarene Compound (23)

A 100-milliliter four-neck flask equipped with a stirrer, a thermometer, a dropping funnel, and a reflux condenser tube was charged with 3.61 g (91.3 mmol) of sodium hydride, and mineral oil was removed by washing with 40 mL of hexane. The hexane solution was removed with a syringe. Another hexane washing was performed. 20 mL of dimethylformamide was then added, and the solution was stirred under ice-cold conditions. A solution of the intermediate (B-1) (4.0 g, 6.8 mmol) in 20 mL of dimethylformamide prepared separately was added dropwise from a dropping funnel to the flask for 30 minutes. After the completion of the dropwise addition, the ice bath was removed. The solution was stirred at room temperature for 30 minutes and was then cooled again in the ice bath. 1,1,1,2,2-pentafluoro-4-iodobutane (22.5 g, 82.1 mmol) was added dropwise from a dropping funnel for 20 minutes. After the completion of the dropwise addition, the ice bath was removed, and the reaction mixture was stirred at room temperature for 20 hours. The reaction mixture was poured into a 200-mL beaker containing ice to terminate the reaction. Concentrated hydrochloric acid was added until the pH of the aqueous layer was 2 or less. 100 mL of chloroform was added to the mixture. After stirring for a while, the mixture was transferred to a separatory funnel to separate the organic layer. 80 mL of chloroform was then added to the aqueous layer to extract organic components. The extraction was performed two times. The organic layer was entirely transferred to a separatory funnel. The organic layer was then washed with 100 mL of water three times, with 60 mL of saturated aqueous sodium hydrogen carbonate once, and with 60 mL of saturated saline once, in this order. The organic layer was dried over anhydrous magnesium sulfate. The solution was filtered to collect the organic phase. The solvent was then evaporated with an evaporator. An orange liquid was obtained. The liquid was purified by silica gel column chromatography. 7.15 g (yield 90%) of a calixarene compound (23) represented by the following structural formula (z) was obtained.

[Chem. 40]

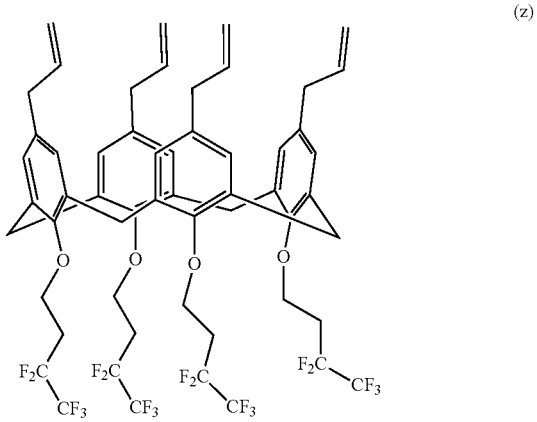

(z)

Example 24 Production of Calixarene Compound (24)

Trifluoromethanesulfonic acid (50 g) was charged into a 200-mL four-neck flask equipped with a stirrer, a thermometer, a dropping funnel, and a reflux condenser tube. The intermediate (A-1) (7 g, 16.5 mmol) was added in portions and was dissolved. 4,4,5,5,5-pentafluoropentanoyl chloride (16.7 g, 79.2 mmol) synthesized by a method described in Japanese Patent No. 4856310 was added dropwise to the resulting orange solution for 20 minutes or more. Upon the dropwise addition, a hydrochloric acid gas was generated. After the completion of the dropwise addition, the reaction mixture was stirred at room temperature for 6 hours. The reaction mixture was poured into ice to terminate the reaction. An orange solid precipitated was then filtered off and was washed with a large amount of water. The resulting solid was dissolved in 200 mL of ethyl acetate and was transferred to a separatory funnel. 100 mL of water was added to wash the organic layer. The washing was performed three times. The organic layer was then washed with 100 mL of saturated saline and was dried over anhydrous magnesium sulfate. The solution was filtered to collect the organic phase. The solvent was then evaporated with an evaporator. An orange solid was obtained. 100 mL of chloroform was added to the solid, and a mixture of white solid and orange liquid was obtained. The white solid was filtered off and was dried under vacuum. Washing with chloroform was performed again. 7.4 g (yield 40%) of a calixarene compound (24) represented by the following structural formula (aa) was obtained.

[Chem. 41]

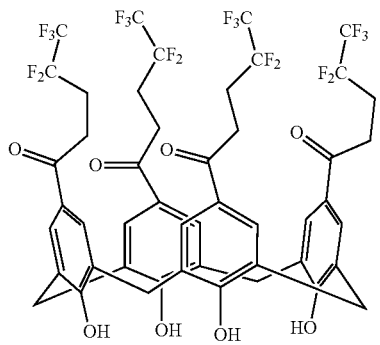

(aa)

[Chem. 42]

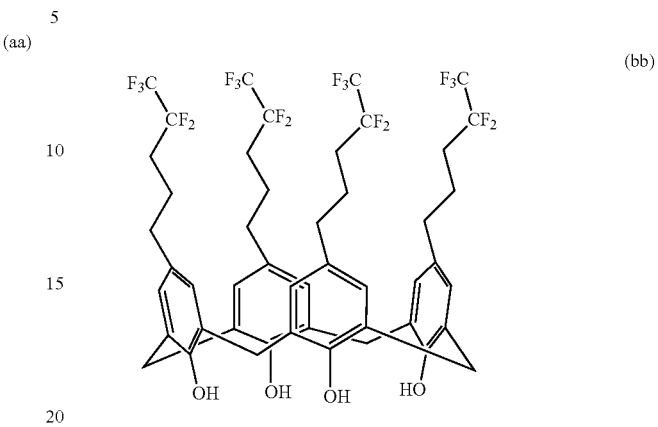

(bb)

Example 26 Production of Calixarene Compound (26)

6.47 g (yield 85%) of a calixarene compound (26) represented by the following structural formula (cc) was produced in the same manner as in Example 2 except that the calixarene compound (25) (6 g, 5.63 mmol) was used instead of the calixarene compound (1) in Example 2.

Example 25 Production of Calixarene Compound (25)

Trifluoroacetic acid (270 mL) was charged into a 500-milliliter four-neck flask equipped with a stirrer, a thermometer, a dropping funnel, and a reflux condenser tube. A calixarene compound (24) (7 g, 6.25 mmol) was then added in portions and was dissolved in the trifluoroacetic acid. Triethylsilane (14.5 g, 125 mmol) was added dropwise to the resulting orange solution from a dropping funnel. After the completion of the dropwise addition, the solution, which turned to clear and colorless, was stirred at room temperature for 72 hours. The reaction mixture was poured into water to terminate the reaction. A brown solid precipitated was then filtered off and was washed with a large amount of water. The resulting solid was dissolved in 200 mL of ethyl acetate and was transferred to a separatory funnel. 100 mL of water was added to wash the organic layer. The organic layer was temporarily transferred to a beaker. 100 mL of water was added to the organic layer. The organic layer was neutralized with solid sodium hydrogen carbonate. The neutralized solution was entirely transferred to a separatory funnel to separate the organic layer. 100 mL of ethyl acetate was added to the aqueous layer to extract organic components. The extraction was performed two times. The organic layer was entirely transferred to a separatory funnel, was washed once with 100 mL of saturated saline, and was dried over anhydrous magnesium sulfate. The solution was filtered to collect the organic phase. The solvent was then evaporated with an evaporator. A brown solid was obtained. The solid was purified by silica gel column chromatography. 6.0 g (yield 90%) of a calixarene compound (25) represented by the following structural formula (bb) was obtained.

[Chem. 43]

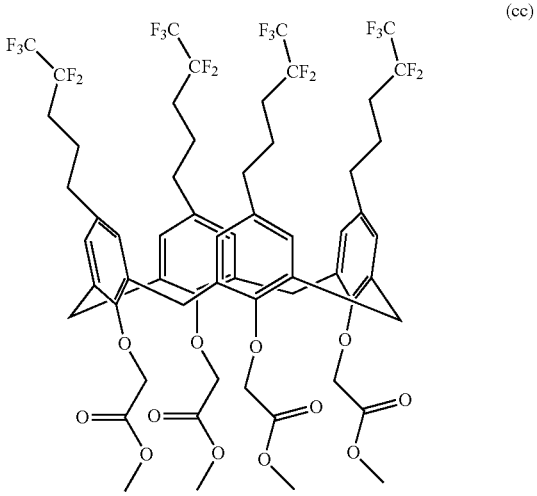

(cc)

Example 27 Production of Calixarene Compound (27)

4.12 g (yield 75%) of a calixarene compound (27) represented by the following structural formula (dd) was produced in the same manner as in Example 3 except that the calixarene compound (26) (6 g, 4.43 mmol) was used instead of the calixarene compound (2).

[Chem. 44]

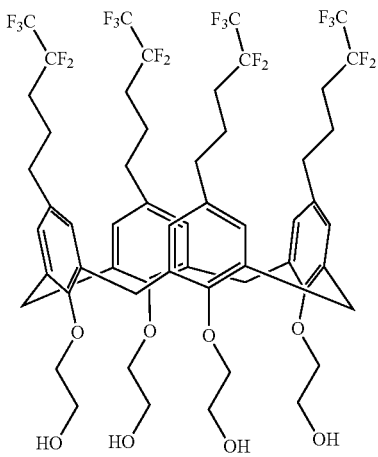

(dd)

Example 28 Production of Calixarene Compound (28)

2.81 g (yield 60%) of a calixarene compound (28) represented by the following structural formula (ee) was produced in the same manner as in Example 18 except that the calixarene compound (27) (4 g, 3.22 mmol) was used instead of the calixarene compound (3).

[Chem. 45]

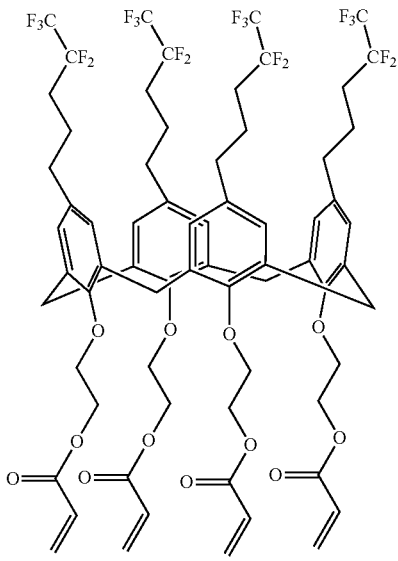

(ee)

Production Example 1 Production of (Meth)acrylate Resin with Silicone Chain (R5-1)

110.8 g of a silicone resin ("KR-500" manufactured by Shin-Etsu Chemical Co., Ltd., alkoxy group content: 28% by mass), 58.1 g of 2-hydroxyethyl acrylate, and 0.034 g of para-toluenesulfonic acid monohydrate were mixed and heated to 120° C. The mixture was allowed to react for 3 hours with stirring while methanol produced by a condensation reaction was evaporated. 153.9 g of a (meth)acrylate resin with a silicone chain (R5-1) was obtained. The (meth)acrylate resin with a silicone chain (R5-1) had a weight-average molecular weight (Mw) of 1,650.

Examples 29 to 74 and Comparative Examples 1 and 2

Curable compositions and cured products were produced as described below and were subjected to various evaluations. Tables 1 to 5 show the evaluation results.

<Production of Curable Composition>

The components in the following tables were mixed and diluted to a non-volatile content of 50% by mass with propylene glycol monomethyl ether acetate to produce a curable composition.

The details of each component in the tables are described below. The composition of each component is expressed in parts by mass.

(R1-1): ethylene oxide modified ortho-phenylphenol acrylate ("Aronix M-106" manufactured by Toagosei Co., Ltd., average number of repeating units of ethylene oxide chain per molecule=1)

(R2-1): trimethylolpropane triacrylate ("Viscoat #295" manufactured by Osaka Organic Chemical Industry Ltd.)

(R3-1): tricyclodecane dimethanol diacrylate ("NKester A-DCP" manufactured by Shin Nakamura Chemical Co., Ltd.)

(R4-1): a compound represented by the following structural formula ("OGSOL EA-0200" manufactured by Osaka Gas Chemicals Co., Ltd.)

[Chem. 46]

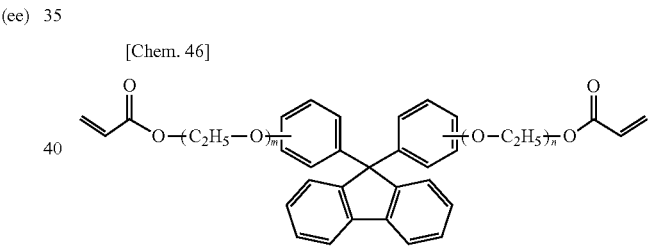

(wherein the sum of m and n is 2 on average)

(R5-1): (meth)acrylate resin with a silicone chain (R5-1) produced in Production Example 1 photopolymerization initiator (1): "Irgacure 369" manufactured by BASF photopolymerization initiator (2): "Irgacure 184" manufactured by BASF photopolymerization initiator (3): "Irgacure 379EG" manufactured by BASF photopolymerization initiator (4): "CPI-100P" manufactured by San-Apro Ltd.

EVALUATION OF APPLICABILITY

A curable composition was applied to a silicon wafer substrate by spin coating to a film thickness of 1.0 μm and was dried on a hot plate at 110° C. for 60 seconds. The resulting film was visually rated according to the following criteria.

A: A smooth film was formed without cissing.

B: A smooth film was not formed due to cissing or the like.

<Evaluation of Mold Releasability>

An alternative evaluation was performed with a texture analyzer as described below.

A glass plate was fixed to a texture analyzer ("TA.XT Plus" manufactured by Stable Micro Systems) with a substrate fixture. 1 µL of the curable composition was dropped on the glass plate, and an indenter with a glass bead was brought into contact with the curable composition at a load of 10 g. In a nitrogen atmosphere, the curable composition was exposed to light at 300 mJ/cm$^2$ from the back side of the glass plate using an LED light source with a peak wavelength of 365±5 nm. The maximum tensile load (MPa) was measured when the indenter was pulled up at a speed of 0.01 mm/s. This procedure was performed five times, and the average of three values excluding the maximum value and the minimum value was used for rating.

<Production of Cured Product>

A curable composition was applied to a silicon wafer substrate by spin coating to a film thickness of 1.0 µm and was dried on a hot plate at 110° C. for 60 seconds. In a nitrogen atmosphere, the curable composition was exposed to light at 500 mJ/cm$^2$ using an LED light source with a peak wavelength of 365±5 nm, thereby forming a cured film.

<Measurement of Water Contact Angle>

The water contact angle on the cured film was measured five times with an automated contact angle measuring device ("OCA40" manufactured by Dataphysics) by the sessile drop method in the air according to JIS R 1257:1999 and was averaged for rating.

<Production of Patterned Sample>

A curable composition was applied to a silicon wafer substrate by spin coating to a film thickness of 1.0 µm and was dried on a hot plate at 110° C. for 60 seconds. The silicon wafer substrate was placed on a lower stage in nanoimprint equipment ("X300" manufactured by SCIVAX). A quartz mold ("NIM PHH-100" manufactured by NTT Advanced Technology Corporation, duty ratio: 1/1, 1/2, 1/3, hole width: 70 to 3000 nm, groove depth: 200 nm, cleaned with UV ozone cleaner, water contact angle on mold surface: less than 10 degrees) was then placed on an upper stage of the nanoimprint equipment. The upper stage was lowered to bring the mold into contact with the curable composition. The pressure was increased to 100 N in 10 seconds at room temperature and was held for 30 seconds to remove bubbles from the film. The curable composition was exposed to light at 500 mJ/cm$^2$ through the mold using an LED light source with a peak wavelength of 365±5 nm. The upper stage was then raised at a speed of 1 mm/min to separate the mold, thus preparing a sample. The mold was continuously used without cleaning, and 10 samples were prepared by the same method. The 10th sample was subjected to various evaluation tests. The curable composition produced in Comparative Example 2 did not form a smooth film on the silicon wafer and could not be subjected to the evaluation tests.

<Presence of Pattern Collapse>

The presence of pattern collapse in the patterned sample at a duty ratio of 1/1 in a region with a minimum hole width of 70 nm×70 nm was observed with a scanning electron microscope and was rated according to the following criteria.

A: No pattern collapse was observed.

B: Pattern collapse was observed.

TABLE 1

| Example | 29 | 30 | 31 | 32 | 33 | 34 | 35 | 36 | 37 | 38 |
|---|---|---|---|---|---|---|---|---|---|---|
| Calixarene compound (1) | 1 | 1 | | | | | | | | |
| Calixarene compound (3) | | | 1 | 1 | | | | | | |
| Calixarene compound (5) | | | | | 1 | 1 | | | | |
| Calixarene compound (6) | | | | | | | 1 | 1 | | |
| Calixarene compound (7) | | | | | | | | | 1 | 1 |
| R1-1 | | 50 | | 50 | | 50 | | 50 | | 50 |
| R2-1 | | 10 | | 10 | | 10 | | 10 | | 10 |
| R3-1 | | 25 | | 25 | | 25 | | 25 | | 25 |
| R4-1 | | 15 | | 15 | | 15 | | 15 | | 15 |
| R5-1 | 100 | | 100 | | 100 | | 100 | | 100 | |
| Photopolymerization initiator (1) | 2 | | 2 | | 2 | | 2 | | 2 | |
| Photopolymerization initiator (2) | | 1 | | 1 | | 1 | | 1 | | 1 |
| Photopolymerization initiator (3) | | 2 | | 2 | | 2 | | 2 | | 2 |
| Photopolymerization initiator (4) | | | | | | | | | | |
| Applicability | A | A | A | A | A | A | A | A | A | A |
| Mold releasability [MPa] | 0.04 | 0.06 | 0.05 | 0.06 | 0.09 | 0.08 | 0.07 | 0.06 | 0.09 | 0.09 |
| Water contact angle [°] | 95.2 | 96.2 | 94.1 | 94.2 | 94.5 | 94.7 | 94.1 | 94.0 | 95.1 | 95.2 |
| Presence of pattern collapse | A | A | A | A | A | A | A | A | A | A |

TABLE 2

| Example | 39 | 40 | 41 | 42 | 43 | 44 | 45 | 46 | 47 | 48 |
|---|---|---|---|---|---|---|---|---|---|---|
| Calixarene compound (9) | 1 | 1 | | | | | | | | |
| Calixarene compound (11) | | | 1 | 1 | | | | | | |
| Calixarene compound (12) | | | | | 1 | 1 | | | | |
| Calixarene compound (13) | | | | | | | 1 | 1 | | |
| Calixarene compound (14) | | | | | | | | | 1 | 1 |
| R1-1 | | 50 | | 50 | | 50 | | 50 | | 50 |
| R2-1 | | 10 | | 10 | | 10 | | 10 | | 10 |
| R3-1 | | 25 | | 25 | | 25 | | 25 | | 25 |
| R4-1 | | 15 | | 15 | | 15 | | 15 | | 15 |
| R5-1 | 100 | | 100 | | 100 | | 100 | | 100 | |

TABLE 2-continued

| Example | 39 | 40 | 41 | 42 | 43 | 44 | 45 | 46 | 47 | 48 |
|---|---|---|---|---|---|---|---|---|---|---|
| Photopolymerization initiator (1) | 2 |  | 2 |  | 2 |  | 2 |  | 2 |  |
| Photopolymerization initiator (2) |  | 1 |  | 1 |  | 1 |  | 1 |  | 1 |
| Photopolymerization initiator (3) |  | 2 |  | 2 |  | 2 |  | 2 |  | 2 |
| Photopolymerization initiator (4) |  |  |  |  |  |  |  |  |  |  |
| Applicability | A | A | A | A | A | A | A | A | A | A |
| Mold releasability [MPa] | 0.09 | 0.09 | 0.13 | 0.12 | 0.15 | 0.15 | 0.10 | 0.10 | 0.14 | 0.15 |
| Water contact angle [°] | 93.6 | 93.8 | 90.1 | 91.8 | 92.1 | 92.6 | 94.1 | 94.6 | 91.9 | 92.0 |
| Presence of pattern collapse | A | A | A | A | A | A | A | A | A | A |

TABLE 3

| Example | 49 | 50 | 51 | 52 | 53 | 54 | 55 | 56 | 57 | 58 |
|---|---|---|---|---|---|---|---|---|---|---|
| Calixarene compound (15) | 1 | 1 |  |  |  |  |  |  |  |  |
| Calixarene compound (16) |  |  | 1 | 1 |  |  |  |  |  |  |
| Calixarene compound (17) |  |  |  |  | 1 | 1 |  |  |  |  |
| Calixarene compound (18) |  |  |  |  |  |  | 1 | 1 |  |  |
| Calixarene compound (19) |  |  |  |  |  |  |  |  | 1 | 1 |
| R1-1 |  | 50 |  | 50 |  | 50 |  | 50 |  | 50 |
| R2-1 |  | 10 |  | 10 |  | 10 |  | 10 |  | 10 |
| R3-1 |  | 25 |  | 25 |  | 25 |  | 25 |  | 25 |
| R4-1 |  | 15 |  | 15 |  | 15 |  | 15 |  | 15 |
| R5-1 | 100 |  | 100 |  | 100 |  | 100 |  | 100 |  |
| Photopolymerization initiator (1) | 2 |  | 2 |  | 2 |  | 2 |  | 2 |  |
| Photopolymerization initiator (2) |  | 1 |  | 1 |  | 1 |  | 1 |  | 1 |
| Photopolymerization initiator (3) |  | 2 |  | 2 |  | 2 |  | 2 |  | 2 |
| Photopolymerization initiator (4) |  |  |  |  |  |  |  |  |  |  |
| Applicability | A | A | A | A | A | A | A | A | A | A |
| Mold releasability [MPa] | 0.08 | 0.09 | 0.12 | 0.11 | 0.14 | 0.13 | 0.15 | 0.15 | 0.12 | 0.12 |
| Water contact angle [°] | 95.5 | 95.7 | 94.5 | 94.7 | 93.3 | 93.7 | 91.3 | 91.5 | 93.9 | 93.9 |
| Presence of pattern collapse | A | A | A | A | A | A | A | A | A | A |

TABLE 4

| Example | 59 | 60 | 61 | 62 | 63 | 64 | 65 | 66 | 67 | 68 |
|---|---|---|---|---|---|---|---|---|---|---|
| Calixarene compound (20) | 1 | 1 |  |  |  |  |  |  |  |  |
| Calixarene compound (21) |  |  | 1 | 1 |  |  |  |  |  |  |
| Calixarene compound (22) |  |  |  |  | 1 | 1 |  |  |  |  |
| Calixarene compound (23) |  |  |  |  |  |  | 1 | 1 |  |  |
| Calixarene compound (24) |  |  |  |  |  |  |  |  | 1 | 1 |
| R1-1 |  | 50 |  | 50 |  | 50 |  | 50 |  | 50 |
| R2-1 |  | 10 |  | 10 |  | 10 |  | 10 |  | 10 |
| R3-1 |  | 25 |  | 25 |  | 25 |  | 25 |  | 25 |
| R4-1 |  | 15 |  | 15 |  | 15 |  | 15 |  | 15 |
| R5-1 | 100 |  | 100 |  | 100 |  | 100 |  | 100 |  |
| Photopolymerization initiator (1) | 2 |  |  |  |  |  | 2 |  | 2 |  |
| Photopolymerization initiator (2) |  | 1 |  | 1 |  | 1 |  | 1 |  | 1 |
| Photopolymerization initiator (3) |  | 2 |  | 2 |  | 2 |  | 2 |  | 2 |
| Photopolymerization initiator (4) |  |  | 4 |  | 4 |  |  |  |  |  |
| Applicability | A | A | A | A | A | A | A | A | A | A |
| Mold releasability [MPa] | 0.14 | 0.15 | 0.05 | 0.06 | 0.05 | 0.09 | 0.12 | 0.12 | 0.15 | 0.13 |
| Water contact angle [°] | 93.9 | 93.9 | 94.3 | 93.8 | 95.0 | 93.1 | 91.5 | 91.8 | 90.8 | 90.5 |
| Presence of pattern collapse | A | A | A | A | A | A | A | A | A | A |

TABLE 5

|  | Example | | | | | | Comparative Example | |
|---|---|---|---|---|---|---|---|---|
|  | 69 | 70 | 71 | 72 | 73 | 74 | 1 | 2 |
| Calixarene compound (25) | 1 | 1 |  |  |  |  |  |  |
| Calixarene compound (27) |  |  | 1 | 1 |  |  |  |  |
| Calixarene compound (28) |  |  |  |  | 1 | 1 |  |  |
| R1-1 |  | 50 |  | 50 |  | 50 |  | 50 |

TABLE 5-continued

|  | Example |  |  |  |  |  | Comparative Example |  |
|---|---|---|---|---|---|---|---|---|
|  | 69 | 70 | 71 | 72 | 73 | 74 | 1 | 2 |
| R2-1 |  | 10 |  | 10 |  | 10 |  | 10 |
| R3-1 |  | 25 |  | 25 |  | 25 |  | 25 |
| R4-1 |  | 15 |  | 15 |  | 15 |  | 15 |
| R5-1 | 100 |  | 100 |  | 100 |  | 100 |  |
| Photopolymerization initiator (1) | 2 |  | 2 |  | 2 |  | 2 |  |
| Photopolymerization initiator (2) |  | 1 |  | 1 |  | 1 |  | 1 |
| Photopolymerization initiator (3) |  | 2 |  | 2 |  | 2 |  | 2 |
| Photopolymerization initiator (4) |  |  |  |  |  |  |  |  |
| Applicability | A | A | A | A | A | A | A | B |
| Mold releasability [MPa] | 0.07 | 0.09 | 0.08 | 0.09 | 0.19 | 0.18 | 0.53 | 0.62 |
| Water contact angle [°] | 94.1 | 94.5 | 94.7 | 94.6 | 90.8 | 91.0 | 87.8 | — |
| Presence of pattern collapse | A | A | A | A | A | A | B | — |

The invention claimed is:

1. A release agent that is a calixarene compound with a molecular structure represented by the following structural formula (1-1) or (1-2):

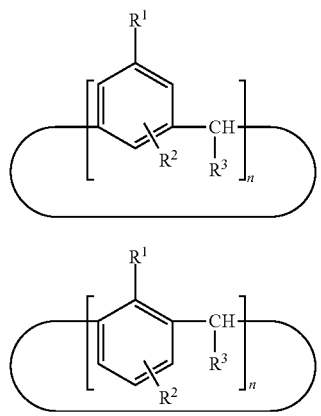

wherein, in structural formula (1-1) and (1-2):

$R^1$ denotes a structural moiety represented by structural formula (2):

wherein, in structural formula (2):

$R^4$ independently denotes a direct bond or an alkylene group having 1 to 6 carbon atoms, $R^F$ denotes a perfluoroalkyl group, and Y denotes a carbonyl group, an oxygen atom, or a sulfur atom;

$R^2$ denotes a structural moiety represented by:

 (3-1)

 (3-2)

 (3-4)

 (3-7)

-continued

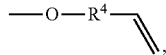 (4-1)

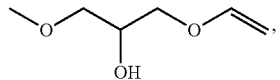 (4-2)

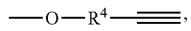 (4-3)

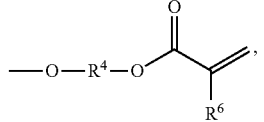 (4-4)

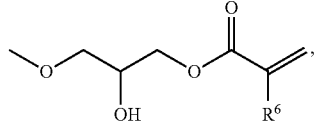 (4-5)

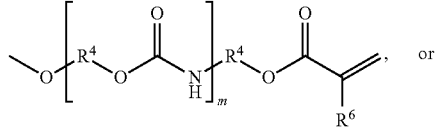 (4-6)

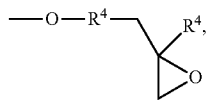 (4-7)

wherein, in structural formula (3-1), (3-2), (3-4), (3-7), (4-1), (4-2), (4-3), (4-4), (4-5), (4-6), or (4-7):

$R^4$ independently denotes an alkylene group having 1 to 6 carbon atoms, $R^5$ independently denotes an alkyl group having 1 to 3 carbon atoms, and $R^6$ denotes a hydrogen atom or a methyl group;

$R^3$ denotes a hydrogen atom, an aliphatic hydrocarbon group that may have a substituent, or an aryl group that may have a substituent; and n denotes an integer in the range of 4 to 10.

2. The release agent that is the calixarene compound according to claim 1, wherein $R^2$ denotes a structural moiety with a vinyl group, a vinyloxy group, an ethynyl group, an ethynyloxy group, a (meth)acryloyl group, or a (meth)acryloyloxy group.

3. A curable composition comprising: the release agent that is the calixarene compound according to claim 1; and a curable resin material.

4. A nanoimprint lithography resin material comprising the release agent that is the calixarene compound according to claim 1.

5. A curable composition comprising: the release agent that is the calixarene compound according to claim 2; and a curable resin material.

6. A nanoimprint lithography resin material comprising the release agent that is the calixarene compound according to claim 2.

* * * * *